US007723497B2

United States Patent

(12) United States Patent
Gross et al.

(10) Patent No.: US 7,723,497 B2
(45) Date of Patent: May 25, 2010

(54) HUMAN IPLA$_{2\epsilon}$

(75) Inventors: Richard W. Gross, Chesterfield, MO (US); Christopher M. Jenkins, Saint Louis, MO (US)

(73) Assignee: Washington University in St. Louis, St. Louis, MO (US)

( * ) Notice: Subject to any disclaimer, the term of this patent is extended or adjusted under 35 U.S.C. 154(b) by 1091 days.

(21) Appl. No.: 11/010,558

(22) Filed: Dec. 13, 2004

(65) Prior Publication Data

US 2005/0227323 A1 Oct. 13, 2005

Related U.S. Application Data

(60) Provisional application No. 60/528,951, filed on Dec. 11, 2003.

(51) Int. Cl.
*C07H 21/04* (2006.01)
*C12P 21/00* (2006.01)

(52) U.S. Cl. .................................... 536/23.1; 435/69.1

(58) Field of Classification Search ....................... None
See application file for complete search history.

(56) References Cited

U.S. PATENT DOCUMENTS

2007/0042945 A1 * 2/2007 Bodary et al. ................. 514/12

FOREIGN PATENT DOCUMENTS

WO WO 02/074961 A1 * 9/2002

OTHER PUBLICATIONS

U. K. Laemmli, "Nature," Cleavage of Structural Proteins during the Assembly of the Head of Bacteriophage T4, 1970, 680-685 pgs., vol. 227., Nature, US.

Sylvain Baulande et al., "The Journal of Biological Chemistry," Adiponutrin, a Transmembrane Protein Corresponding to a Novel Dietary - and Obesity - linked mRNA Specifically Expressed in the Adipose Lineage, Jun. 28, 2001, 33336-33444 pgs., vol. 276, No. 36, JBC Papers in Press, US.

Lea Reshef et al., "The Journal of Biological Chemistry," Glyceroneogenesis and the Triglyceride/Fatty Acid Cycle, Jun. 4, 2003, 30413-30416 pgs., vol. 278, No. 33, JBC Papers in Press, US.

Jun-Ichi Osuga et al., "Proc. Natl. Acad. Sci.," Targeted Disruption of Hormone-Sensitive Lipase Results in Male Sterility and Adipocyte Hypertrophy, but Not in Obesity, Jan. 18, 2000, 787-792 pgs., vol. 97, No. 2, Proc. Natl. Acad. Sci., US.

Christopher M. Jenkins et al., "The Journal of Biological Chemistry," Identification, Cloning, Expression, and Purification of Three Novel Human Calcium-independent Phospholipase A2 Family Members Possessing Triacylglycerol Lipase and Aclglycerol Transacylase Activities, Sep. 10, 2004, 48968-48975 pgs., vol. 279, No. 47, JBC Papers in Press, US.

Susan C. Frost and M. Daniel Lane, "The Journal of Biological Chemistry," Evidence for the Involvement of Vicinal Sulfhydryl Groups in Insulin-activated Hexose Transport by 3T3-L1 Adipocytes, 1985, 2646-2652 pgs., vol. 260, No. 5, The American Society of Biological Chemists, Inc., US.

Lahoucine Izem and Richard E. Morton, "The Journal of Biological Chemistry," Cholestryl Ester Transfer Protein Biosynthesis and Cellular Cholesterol Homeostasis Are Tightly Interconnected, May 14, 2001, 26534-26541 pgs., vol. 276, No. 28, JBC Papers in Press, US.

Richard Lehner and Arnis Kuksis, "The Journal of Biological Chemistry," Triacyglycerol Synthesis by an sn-1,2 (2.3) - Diacyglycerol Transacylase from Rat Intestinal Microsomes, 1993, 8781-8786 pgs., vol. 268, No. 12, The American Society of Biological Chemists, Inc., US.

Dagmar A. Polson and Mary P. Thompson, "The Journal of Nutritional Biochemistry", Macronutrient Composition of the Diet Differentially Affects Leptin and Adiponutrin mRNA Expression in Response to Meal Feeding, 2004, 242-246 pgs., vol. 15, Elsevier.

Guenter Haemmerle et al., "The Journal of Biological Chemistry", Hormone-Sensitive Lipase Deficiency in Mice Causes Diglyceride Accumulation in Adipose Tissue, Muscle, and Testis, Nov. 20, 2001, 4806-4815 pgs., vol. 277, No. 7, JBC Papers in Press, US.

Hiroaki Okazaki et al., "Diabetes," Lipolysis in the Absence of Hormone-Sensitive Lipase, Evidence for a Common Mechanism Regulating Distinct Lipases, Dec. 2002, 3368-3375 pgs., vol. 51, Diabetes, US.

Shu Pei Wang et al., "Obesity Research," The Adipose Tissue Phenotype of Hormone-Sensitive Lipase Deficiency in Mice, Feb. 2001, 119-128 pgs., vol. 9, No. 2, Obesity Research, US.

Dagmar A. Polson and Mary P. Thompson, "Biochemical and Biophysical Research Communications," Adiponutrin mRNA Expression in White Adipose Tissue is Rapidly Induced by Meal-Feeding a High-Sucrose Diet, 2003, 261-266 pgs., vol. 301, Academic Press, US.

Dagmar A. Polson and Mary P. Thompson, "Horm. Metab. Res.," Adiponutrin Gene Expression in 3T3-L1 Adipocytes is Downregulated by Troglitazone, 2003, 508-510 pgs., vol. 35, Issue No. 0018-5043.

Jordi Folch et. al., "The Journal of Biological Chemistry," A Simple Method for the Isolation and Purification of Total Lipides From Animal Tissues, 1957, 497-509 pgs., vol. 226.

* cited by examiner

*Primary Examiner*—Anand U Desai
(74) *Attorney, Agent, or Firm*—Armstrong Teasdale LLP

(57) ABSTRACT

A novel function phospholipase $A_2$, referred to herein as calcium-independent phospholipase $A_{2\epsilon}$ (iPLA$_{2\epsilon}$) having SEQ ID NO: 1 and SEQ ID NO: 2, and nucleic acid sequences (SEQ ID NO: 3 and SEQ ID NO: 4) encoding and expressing iPLA$_{2\epsilon}$ is disclosed. This novel enzyme has been isolated and characterized and is involved in the catalysis and hydrolysis of lipids cycling in a living cell biosystem. In an embodiment, the iPLA$_{2\epsilon}$ polypeptide is encoded and expressed by an isolated nucleic acid molecule comprising a set of iPLA$_{2\epsilon}$ polynucleotides. In one aspect, an isolated and characterized gene comprises a polynucleotide having a sequence shown in SEQ ID NO: 3 and SEQ ID NO: 4.

12 Claims, 17 Drawing Sheets

Human Adiponutrin ($iPLA_2\varepsilon$)

Sequence ID= AK025665 (nucleotide); reference SNP ID = rs2294918(g)

```
SEQ ID 3: atgtacgacgcagagcgcggctggagcttgtccttcgcgggctgcggcttcctgggcttc
SEQ ID 1:  M  Y  D  A  E  R  G  W  S  L  S  F  A  G  C  G  F  L  G  F
          taccacgtcggggcgacccgctgcctgagcgagcacgccccgcacctcctccgcgacgcg
           Y  H  V  G  A  T  R  C  L  S  E  H  A  P  H  L  L  R  D  A
          cgcatgttgttcggcgcttcggccggggcgttgcactgcgtcggcgtcctctccggtatc
           R  M  L  F  G  A  S  A  G  A  L  H  C  V  G  V  L  S  G  I
                             |
                             O - R
          ccgctggagcagactctgcaggtcctctcagatcttgtgcggaaggccaggagtcggaac
           P  L  E  Q  T  L  Q  V  L  S  D  L  V  R  K  A  R  S  R  N
          attggcatcttccatccatccttcaacttaagcaagttcctccgacagggtctctgcaaa
           I  G  I  F  H  P  S  F  N  L  S  K  F  L  R  Q  G  L  C  K
          tgcctcccggccaatgtccaccagctcatctccggcaaaataggcatctctcttaccaga
           C  L  P  A  N  V  H  Q  L  I  S  G  K  I  G  I  S  L  T  R
          gtgtctgatggggaaaacgttctggtgtctgactttcggtccaaagacgaagtcgtggat
           V  S  D  G  E  N  V  L  V  S  D  F  R  S  K  D  E  V  V  D
          gccttggtatgttcctgcttcatccccttctacagtggccttatccctccttccttcaga
           A  L  V  C  S  C  F  I  P  F  Y  S  G  L  I  P  P  S  F  R
          ggcgtgcgatatgtggatggaggagtgagtgacaacgtacccttcattgatgccaaaaca
           G  V  R  Y  V  D  G  G  V  S  D  N  V  P  F  I  D  A  K  T
          accatcaccgtgtcccccttctatggggagtacgacatctgccctaaagtcaagtccacg
           T  I  T  V  S  P  F  Y  G  E  Y  D  I  C  P  K  V  K  S  T
          aactttcttcatgtggacatcaccaagctcagtctacgcctctgcacagggaacctctac
           N  F  L  H  V  D  I  T  K  L  S  L  R  L  C  T  G  N  L  Y
          cttctctcgagagcttttgtcccccggatctcaaggtgctgggagagatatgccttcga
           L  L  S  R  A  F  V  P  P  D  L  K  V  L  G  E  I  C  L  R
          ggatatttggatgcattcaggttcttggaagagaagggcatctgcaacaggccccagcca
           G  Y  L  D  A  F  R  F  L  E  E  K  G  I  C  N  R  P  Q  P
          ggcctgaagtcatcctcagaagggatggatcctgaggtcgccatgcccagctgggcaaac
           G  L  K  S  S  S  E  G  M  D  P  E  V  A  M  P  S  W  A  N
          atgagtctggattcttccccggagtcggctgccttggctgtgaggctggagggagatgag
           M  S  L  D  S  S  P  E  S  A  A  L  A  V  R  L  E  G  D  E
          ctgctagaccacctgcgtctcagcatcctgccctgggatgagagcatcctggacaccctc
           L  L  D  H  L  R  L  S  I  L  P  W  D  E  S  I  L  D  T  L
          tcgcccaggctcgctacagcactgagtgaagaaatgaaagacaaaggtggatacatgagc
           S  P  R  L  A  T  A  L  S  E  E  M  K  D  K  G  G  Y  M  S
          aagatttgcaacttgctacccattaggataatgtcttatgtaatgctgccctgtaccctg
           K  I  C  N  L  L  P  I  R  I  M  S  Y  V  M  L  P  C  T  L
          cctgtggaatctgccattgcgattgtccagagactggtgacatggcttccagatatgccc
           P  V  E  S  A  I  A  I  V  Q  R  L  V  T  W  L  P  D  M  P
          gacgatgtcctgtggttgcagtgggtgacctcacaggtgttcactcgagtgctgatgtgt
           D  D  V  L  W  L  Q  W  V  T  S  Q  V  F  T  R  V  L  M  C
          ctgctccccgcctccaggtcccaaatgccagtgagcagccaacaggcctccccatgcaca
           L  L  P  A  S  R  S  Q  M  P  V  S  S  Q  Q  A  S  P  C  T
          cctgagcaggactggccctgctggactccctgctcccccgagggctgtccagcagagacc
           P  E  Q  D  W  P  C  W  T  P  C  S  P [E] G  C  P  A  E  T
          aaagcagaggccaccccgcggtccatcctcaggtccagcctgaacttcttcttgggcaat
           K  A  E  A  T  P  R  S  I  L  R  S  S  L  N  F  F  L  G  N
          aaagtacctgctggtgctgaggggctctccacctttcccagtttttcactagagaagagt
           K  V  P  A  G  A  E  G  L  S  T  F  P  S  F  S  L  E  K  S
          ctgtga
           L  -
```

Fig. 3A

Human Adiponutrin (iPLA$_2$ε)

Sequence ID= AL138578.2 (nucleotide); NP_079501 (protein);

reference SNP ID = rs2294918(a)

```
SEQ ID 4: atgtacgacgcagagcgcggctggagcttgtccttcgcgggctgcggcttcctgggcttc
SEQ ID 2:  M  Y  D  A  E  R  G  W  S  L  S  F  A  G  C  G  F  L  G  F
          taccacgtcggggcgacccgctgcctgagcgagcacgccccgcacctcctccgcgacgcg
           Y  H  V  G  A  T  R  C  L  S  E  H  A  P  H  L  L  R  D  A
          cgcatgttgttcggcgcttcggccggggcgttgcactgcgtcggcgtcctctccggtatc
           R  M  L  F  G  A  S  A  G  A  L  H  C  V  G  V  L  S  G  I
                          |
                          O - R
          ccgctggagcagactctgcaggtcctctcagatcttgtgcggaaggccaggagtcggaac
           P  L  E  Q  T  L  Q  V  L  S  D  L  V  R  K  A  R  S  R  N
          attggcatcttccatccatccttcaacttaagcaagttcctccgacagggtctctgcaaa
           I  G  I  F  H  P  S  F  N  L  S  K  F  L  R  Q  G  L  C  K
          tgcctcccggccaatgtccaccagctcatctccggcaaaataggcatctctcttaccaga
           C  L  P  A  N  V  H  Q  L  I  S  G  K  I  G  I  S  L  T  R
          gtgtctgatggggaaaacgttctggtgtctgactttcggtccaaagacgaagtcgtggat
           V  S  D  G  E  N  V  L  V  S  D  F  R  S  K  D  E  V  V  D
          gccttggtatgttcctgcttcatccccttctacagtggccttatccctccttccttcaga
           A  L  V  C  S  C  F  I  P  F  Y  S  G  L  I  P  P  S  F  R
          ggcgtgcgatatgtggatggaggagtgagtgacaacgtacccttcattgatgccaaaaca
           G  V  R  Y  V  D  G  G  V  S  D  N  V  P  F  I  D  A  K  T
          accatcaccgtgtccccttctatggggagtacgacatctgccctaaagtcaagtccacg
           T  I  T  V  S  P  F  Y  G  E  Y  D  I  C  P  K  V  K  S  T
          aactttcttcatgtggacatcaccaagctcagtctacgcctctgcacagggaacctctac
           N  F  L  H  V  D  I  T  K  L  S  L  R  L  C  T  G  N  L  Y
          cttctctcgagagcttttgtccccccggatctcaaggtgctgggagagatatgccttcga
           L  L  S  R  A  F  V  P  P  D  L  K  V  L  G  E  I  C  L  R
          ggatatttggatgcattcaggttcttggaagagaagggcatctgcaacaggccccagcca
           G  Y  L  D  A  F  R  F  L  E  E  K  G  I  C  N  R  P  Q  P
          ggcctgaagtcatcctcagaagggatggatcctgaggtcgccatgcccagctgggcaaac
           G  L  K  S  S  S  E  G  M  D  P  E  V  A  M  P  S  W  A  N
          atgagtctggattcttccccggagtcggctgccttggctgtgaggctggagggagatgag
           M  S  L  D  S  S  P  E  S  A  A  L  A  V  R  L  E  G  D  E
          ctgctagaccacctgcgtctcagcatcctgccctgggatgagagcatcctggacaccctc
           L  L  D  H  L  R  L  S  I  L  P  W  D  E  S  I  L  D  T  L
          tcgcccaggctcgctacagcactgagtgaagaaatgaaagacaaaggtggatacatgagc
           S  P  R  L  A  T  A  L  S  E  E  M  K  D  K  G  G  Y  M  S
          aagatttgcaacttgctacccattaggataatgtcttatgtaatgctgccctgtaccctg
           K  I  C  N  L  L  P  I  R  I  M  S  Y  V  M  L  P  C  T  L
          cctgtggaatctgccattgcgattgtccagagactggtgacatggcttccagatatgccc
           P  V  E  S  A  I  A  I  V  Q  R  L  V  T  W  L  P  D  M  P
          gacgatgtcctgtggttgcagtgggtgacctcacaggtgttcactcgagtgctgatgtgt
           D  D  V  L  W  L  Q  W  V  T  S  Q  V  F  T  R  V  L  M  C
          ctgctccccgcctccaggtcccaaatgccagtgagcagccaacaggcctccccatgcaca
           L  L  P  A  S  R  S  Q  M  P  V  S  S  Q  Q  A  S  P  C  T
          cctgagcaggactggccctgctggactccctgctcccccaagggctgtccagcagagacc
           P  E  Q  D  W  P  C  W  T  P  C  S  P [K] G  C  P  A  E  T
          aaagcagaggccaccccgcggtccatcctcaggtccagcctgaacttcttcttgggcaat
           K  A  E  A  T  P  R  S  I  L  R  S  S  L  N  F  F  L  G  N
          aaagtacctgctggtgctgaggggctctccacctttcccagtttttcactagagaagagt
           K  V  P  A  G  A  E  G  L  S  T  F  P  S  F  S  L  E  K  S
          ctgtga
           L  -
```

Fig. 3B

Western Analysis of Human Adiponutrin (iPLA$_2$ε(His)$_6$) Expression in Sf9 Cell Cytosol and Membrane Fractions Human Adiponutrin (iPLA$_2$ε(His)$_6$) Catalyzes Triolein Synthesis (Transacylation) from [Oleoyl-1-$^{14}$C]-Mono-olein BEL Modulates the Lipase/Transacylase Activity Ratio of Human Adiponutrin (iPLA$_2$ε(His)$_6$)

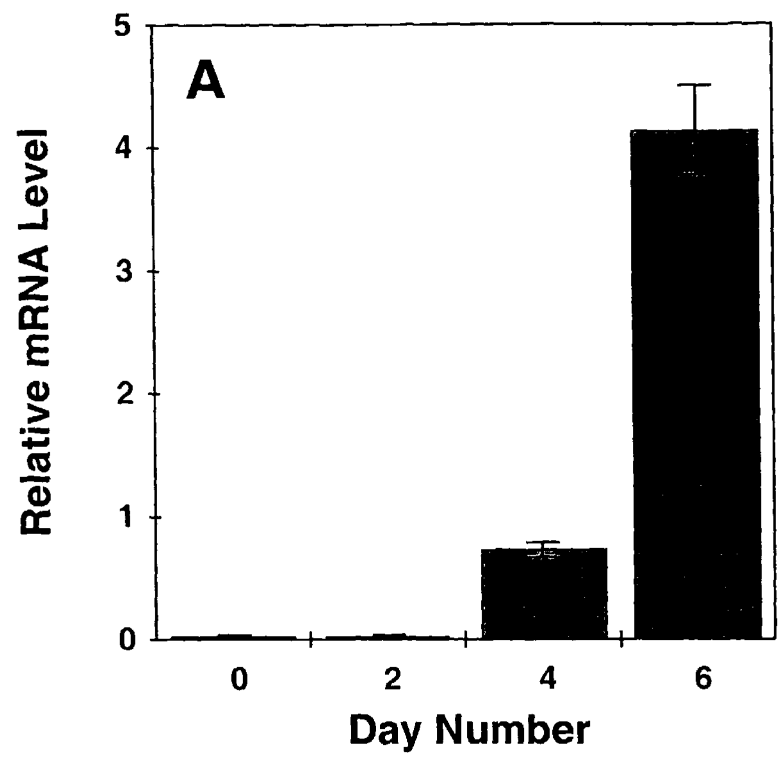
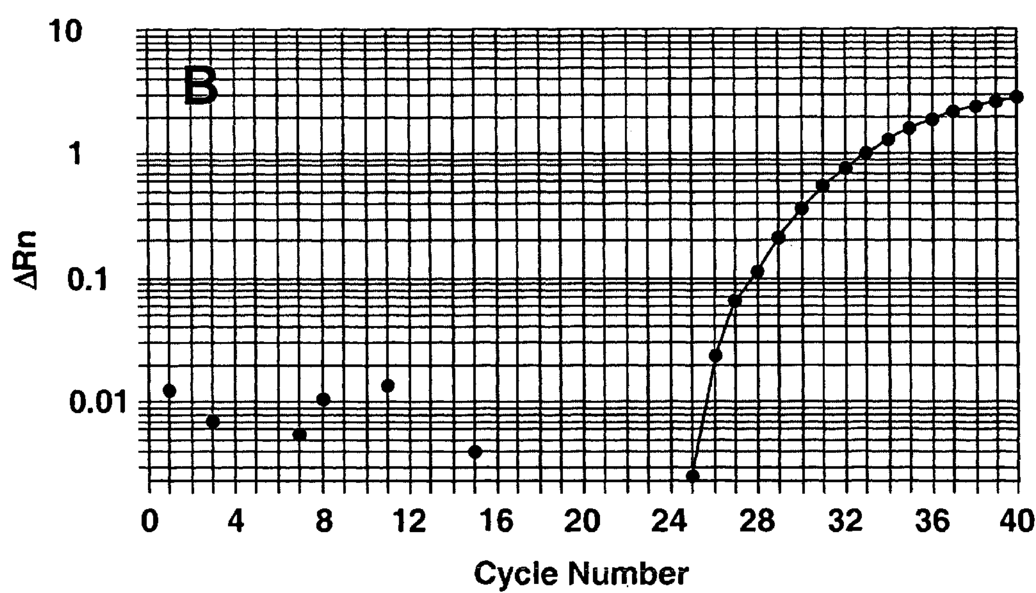
Fig. 12

HUMAN IPLA$_2\epsilon$

CROSS REFERENCE TO RELATED APPLICATIONS

This application claims the benefit of U.S. provisional patent application 60/528,951 filed Dec. 11, 2003 the contents of which are incorporated herein by reference in their entirety.

STATEMENT REGARDING FEDERALLY SPONSORED RESEARCH AND DEVELOPMENT

This research was supported jointly by grants from the National Institutes of Health grants 5P01HL57278-06A1 and 5R01HL41250-10. The government has certain rights in the invention.

FIELD OF THE INVENTION

This discovery relates to phospholipases, lipases and transacylases and to a method for using them. More particularly this discovery relates to a method for screening drugs.

BACKGROUND OF THE INVENTION

Unfortunately in many industrialized countries, the incidence of human obesity is dramatically increasing. Moreover, human obesity is a common and costly nutritional problem in the United States in addition to being a devastating health problem. Obesity is characterized clinically by the accumulation of fat tissue (at times this is referred to as body fat content).

In humans, obesity is usually defined as a body fat content greater than about 25% of the total weight for males, or greater than about 30% of the total weight for females. However obesity exists outside those numbers too. Regardless of the cause of or extent of obesity, obesity is an ever present problem for Americans. But a fat content greater than about 18% for males and greater than about 22% for females can have untold consequences secondary to several mechanisms and disorders of metabolic function. For example, obesity can have a significant adverse impact on health care costs and provoke a higher risk of numerous illnesses, including heart attacks, strokes and diabetes.

In the case of diabetes, patients can lose limbs, eyesight and kidneys and hearts can fail so the potential results can be catastrophic and deadly.

Without being bound by theory, it is believed that obesity in humans results from an abnormal increase in white adipose tissue mass that occurs due to an increased number of adipocytes (hyperplasia) or from increased lipid mass accumulating in existing adipocytes. Obesity and the associated type two metabolic syndrome along with its clinical sequelae are among the major and the most rapidly increasing (epidemic) medical problems in America. However, to date, a lack of suitable adipocyte specific protein targets has unfortunately hampered progress in the development of effective therapeutic agents to combat the clinical sequelae of obesity.

Despite existing knowledge of the critical role of phospholipases in adipocyte signaling, enhanced clinical methodology and research tool and methods are highly needed for new obesity drugs and new methods for identifying useful drugs to treat obesity and over-weightness. It is highly desired to have knowledge and technology based on the specific types of phospholipases and lipases present in the adipocyte, or their mechanisms of regulation, and determine their natural substrates and roles in anabolic lipid metabolism, catabolic lipid metabolism or both (e.g. triglyceride cycling).

BRIEF DESCRIPTION OF THE INVENTION

This invention relates to phospholipases, lipases and transacylases and more particularly to human calcium independent phospholipase A$_2\epsilon$, hereinafter referred to as and denoted (iPLA$_2\epsilon$, also denoted as iPLA$_2$ epsilon), to nucleic acids expressing iPLA$_2\epsilon$, to the use of iPLA$_2\epsilon$ as a pharmacological target in screening and development of potentially useful anti-obesity drugs and drugs for other sequelae of the metabolic syndrome including at least one of atherosclerosis, diabetes, cancer and hypertension and to an animal model useful for such screening.

In an aspect, the invention provides for the first time an isolated novel, purified, recovered, functional and characterized human phospholipase A$_2$, referred to herein as calcium-independent phospholipases A$_2\epsilon$ (iPLA$_2\epsilon$) having SEQ ID NO: 1 (See FIG. 3A) and SEQ ID NO: 2 (See FIG. 3B), and nucleic acid sequences (SEQ ID NO: 3) and (SEQ ID NO: 4) SNP's thereof encoding and expressing iPLA$_2\epsilon$ activity (See FIG. 3A and 3B). For the first time herein, this novel enzyme(s) has been isolated, recovered, purified and characterized. iPLA$_2\epsilon$ is involved in the catalysis, synthesis and hydrolysis of lipids in a living mammalian cell. Moreover, through the process of transesterification the inventors have discovered that this enzyme iPLA$_2\epsilon$ can catalyze the net anabolic synthesis of triglycerides through a variety of metabolic precursor's (e.g. monoacylglycerol, diacylglycerol and acyl CoA).

In one aspect, the invention is directed to an isolated, recovered, and characterized functional nucleic acid molecule comprising a set of iPLA$_2\epsilon$ polynucleotides. In a further aspect of the iPLA$_2\epsilon$ polynucleotides encode and express an iPLA$_2\epsilon$ polypeptide.

In one aspect, an isolated, recovered, functional, characterized human gene comprises an isolated and characterized polynucleotide having a sequence shown in SEQ ID NO: 3 and SEQ ID NO: 4. (See FIGS. 3A and 3B).

In an aspect, an isolated, recovered, functional, characterized human protein comprises a polypeptide having a sequence shown in SEQ ID NO: 1 and SEQ ID NO: 2 (See FIGS. 3A and 3B).

In an aspect, this discovery comprises a method to successfully measure lipase activity in fat cells and its inhibition by BEL. This discovery provides a useful screening method and research tool to identify useful drugs which can be effectively administered to patients afflicted with diabetes, overweight and obesity.

In an aspect, a method of effectively treating a living mammal to reduce obesity, comprises administering an effective amount iPLA$_2\epsilon$ inhibitor thereto or an agent which changes the lipase transacylases ratio.

In an aspect, a genetically engineered isolated, functional, characterized functional expression vector comprises a functional gene or part of the sequence of a human gene comprising a polynucleotide having a sequence shown in SEQ ID NO: 3 or SEQ ID NO: 4 (FIGS. 3A and 3B). In an aspect, the gene encodes a protein comprising a polypeptide having a sequence shown in SEQ ID NO: 1 or SEQ ID NO: 2 (FIGS. 3A and 3B). In an aspect, the gene is operately linked to a capable viable promoter element.

In another aspect, a method of medically treating a mammal comprises administering an anti-obesity (drug or pharmaceutical) in therapeutically effective amounts as an inhibitor to the living mammal.

In another aspect, a method of effectively medically treating at a clinical level a living mammal and comprises administering a therapeutically effective amount of a compound (drug or pharmaceutical) which inhibits iPLA$_2$ε expression to the mammal or result in a different isoform expression or different enzymatic activity or post-translational modification.

In another aspect, a method of treating obesity, at a clinical situation or level comprising administering an agent which changes the transacylase to lipase ratio in a metabolic setting. In an aspect, the metabolic setting is a living animal or an adequately representative animal model. In an aspect the agent compresses a compound.

In an aspect, a pharmaceutical composition is provided comprising a compound which effectively inhibits or counteracts iPLA$_2$ε expression, activity, hydrolysis or transesterification activity or transesterification in a living mammal such, as a human.

In an aspect, a pharmaceutical kit comprises a container housing a compound which effectively inhibits at least one of iPLA$_2$ε expression, activity or transesterification.

In another embodiment, the present invention is directed to a method of modulating fatty acid utilization in a living patient, In an aspect, the patient is a living human patient. In this aspect, the method comprises intentionally and selectively increasing or decreasing iPLA$_2$ε activity in the patient. Patients in need of such treatment include those patients suffering from one of diabetes and/or obesity. Preferably, this method comprises administering to the patient a substance (compound) in an effective amount which blocks or inhibits expression of iPLA$_2$ε mass or activity.

In an aspect a method of identifying an agent which changes the ratio of transacylase to lipase in a living mammal by administering a compound to a mammal and determining if the transacylase to lipase ratio was changed by lipid analysis and if the ratio was changed then determining that the drug is an anti-obesity drug.

In an aspect, the invention comprises a method for ameliorating at least one symptom of a symptomatology comprising obesity and the clinical manifestations of the type 2 metabolic syndrome in a living human which comprises treating a human cell expressing iPLA$_2$ε in a pharmacologically effective manner with a pharmacologically effective amount of an iPLA$_2$ε expression or enzymatic inhibitor. In an aspect the human body is treated by treating the cells thereof.

A method of treating at least one of an overweight and obese disorders, the method comprises administering to a subject (in need of such treatment) a therapeutically effective amount of composition comprising an inhibitor of human or murine iPLA$_2$ε (adiponutrin).

In an aspect, a method of identifying an anti-obesity drug which comprises administering a drug to an animal and determining if there has been any change in iPLA$_2$ε expression, activity, hydrolysis or transesterification activity or futile cycles and if so determining that the drug is an anti-obesity drug.

In an aspect a method of practicing medicine comprises administering a therapeutic amount of a drug to a living patient at risk for obesity or being obese, the drug being an inhibitor of human adiponutrin (iPLA$_2$ε).

In an aspect a method of providing therapy to a patient in need thereof which comprises administering a drug to a patient at risk for obesity, the drug being an inhibitor of the expression of human adiponutrin (iPLA$_2$ε).

In an aspect a method for treating a diabetic comprises administering a drug to a patient in a pharmacologically effective amount to modulate iPLA$_2$ε expression whereby the insulin requirement of the patient is decreased. In an aspect the patient presents clinically determined symptoms of diabetes.

In an aspect a method of treating diabetes comprises administering a drug in an effective amount to modulate iPLA$_2$ε expression whereby the insulin requirement of the patient is decreased.

In an aspect an antibody which recognizes human iPLA$_{2ε}$ comprises a peptide corresponding to residues 295-310 of human iPLA$_{2ε}$ (CRLEGDELLDHLRLSIL) (SEQ ID NO: 9)

In an aspect an animal model which provides at least one of a genomic target and a pharmacological target respectively comprising iPLA$_2$ε for reactive reception to at least one of a projectile comprising siRNA or from a pharmacological drug administered to the animal model. In an aspect, the animal model is a living tissue representative of a living animal or a sample of a living animal such as tissue. In an aspect, the pharmacological drug is a drug being evaluated.

In an aspect, the present discovery also encompasses genetically engineered cells capable of identifying substances which modulate iPLA$_2$ε expression in a living biosystem cell or in a sample adequately representative thereof. In an aspect, such cells comprise a promoter operably linked to iPLA$_2$ε gene and a reporter gene. This reporter gene preferably encodes an enzyme capable of being detected by at least one of a suitable radiometric, fluorimetric or luminometric assay such as, for example, a reporter sequence encoding a luciferase. In an aspect, the promoter sequence is a baculovirus promoter sequence and the cells are Sf9 cells.

In an aspect, the invention comprises a method for prioritizing the therapeutic capability of a drug's putative efficacy against obesity, comprising administering drugs to a living animal system which is actively expressing iPLA$_2$ε, measuring any modulation of the iPLA$_2$ε expression by a TAG or FFA's/glycerol analysis of an effect and determining if the modulation was an increase or a decrease or no change in iPLA$_2$ε expression level. If the modulation is determined to be a decrease then determining that the drug was effective in inhibiting iPLA$_2$ε, a value is assigned to that modulation and is thereafter compared to the modulation of other drugs. In an aspect, a prioritization is set up by comprising the magnitudes of the various respective modulations and a hierarchy of drugs is established. From this, it is possible to a priority of work on the drugs is determined with a focus on their therapeutic capability.

In an aspect the iPLA$_2$ε can function as a signaling enzyme to control eicosanoid synergies and other lipids and messengers of signal transduction. In an aspect a method of attenuating eicosanoid synergies, lipids and messengers of signal transduction by increasing or decreasing the amount of iPLA$_2$ε present in a living biosystem such as a living mammal.

In an aspect, the discovery comprises a method to utilize the selective cleavage of arachidonic acid containing phospholipids mediated by iPLA$_2$ε to screen for inhibitors which can affect the metabolic syndrome and/or result in a change in the weight status, insulin sensitivity, or inflammatory status of the patient and organs and vessels contained therein.

The present invention also includes a method and research tool useful for identifying substances such as a compound, cell or substance or moiety which modulate iPLA$_2$ε expression. In an aspect, a screening method and research tool herein comprises a screening method comprising contacting a candidate substance with cells capably expressing at least a significant amount of iPLA$_2$ε or a fragment thereof, and measuring the expression of iPLA$_2$ε or a fragment thereof by the cells by an analysis of an effluent for the TAG content determining whether a substance modulated $iPLA_2\epsilon$

BRIEF DESCRIPTION OF THE DRAWINGS

FIG. 3A and FIG. 3B show Nucleotide and Deduced Amino Acid Sequences of Our Human Adiponutrin ($iPLA_2\epsilon$) and variants thereof.

FIG. 12 shows Quantitative PCR or $iPLA_2\epsilon$ Message in Mouse 3T3-L1 Preadipocytes and Human SW872 Liposarcoma Cells.

DETAILED DESCRIPTION OF THE DRAWINGS

Figure 1:
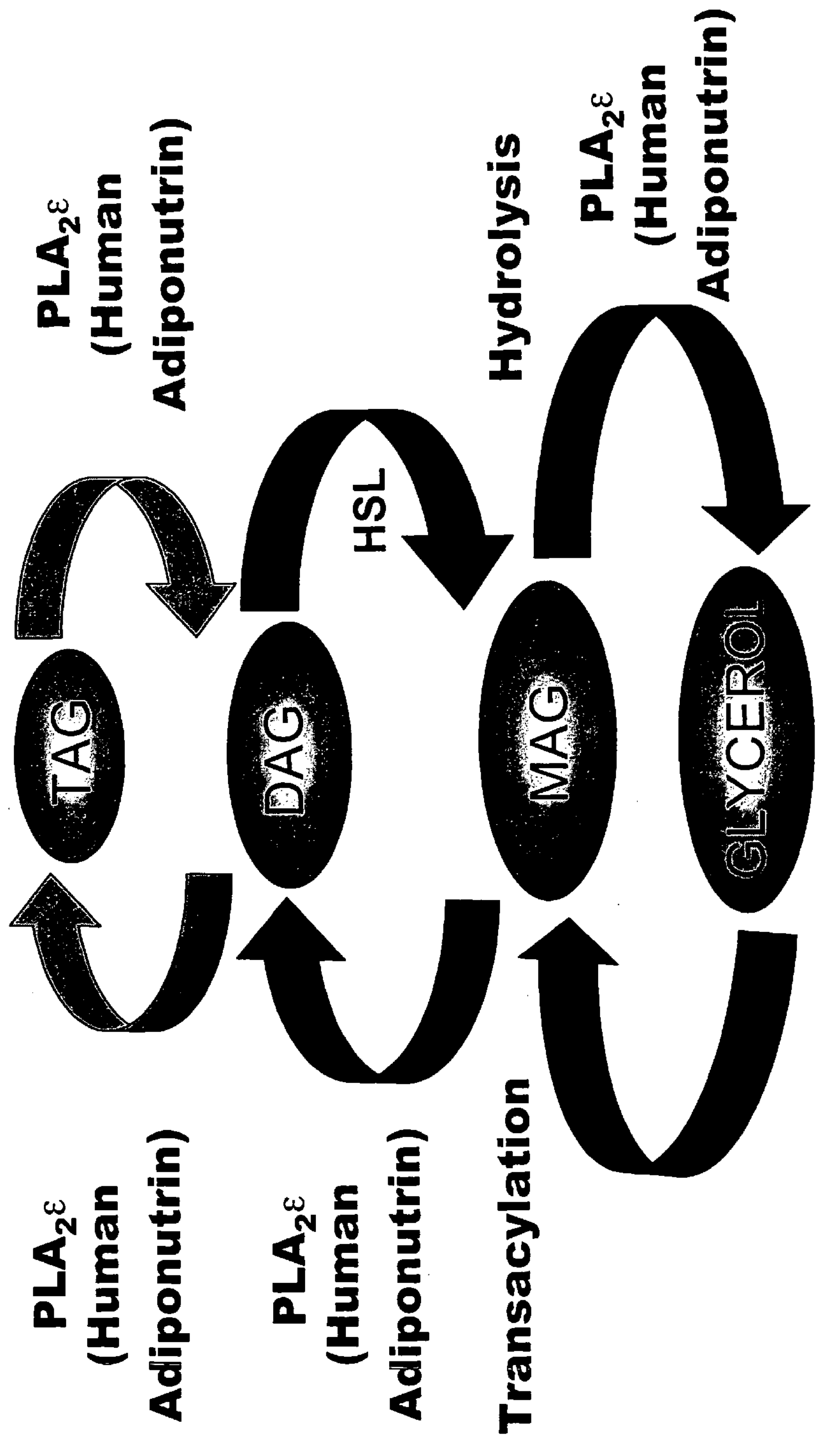
FIG. 1 shows a schematic diagram of Adipocyte Acyl-CoA-Independent Triglyceride Cycling in a living human.

FIG. 1 presents a schematic diagram of Adipocyte Acyl-CoA-Independent Triglyceride Cycling in a living human. The inventors have discovered that acyl-equivalents are stored in the adipocyte primarily in the form of triglycerides which are synthesized by $iPLA_2\epsilon$ (Adiponutrin), $iPLA_2\zeta$, and/or $iPLA_2\eta$ through an acyl-CoA independent transacylation mechanism which transfers fatty acyl moieties from monoacylglycerol (MAG) or diacylglycerol (DAG) acyl-donors to MAG and DAG acyl-acceptor intermediates to and from triacylglycerols (TAG) and that, alternatively, hydrolysis of a single TAG fatty acyl moiety is catalyzed by $iPLA_2\epsilon$ (Adiponutrin), $iPLA_2\zeta$, and/or $iPLA_2\eta$ to form DAG which can then be further degraded to MAG and glycerol by either $iPLA_2\epsilon$ (Adiponutrin), $iPLA_2\zeta$, $iPLA_2\eta$ and/or other intracellular lipases (e.g. hormone sensitive lipase (HSL)).

Figure 2:
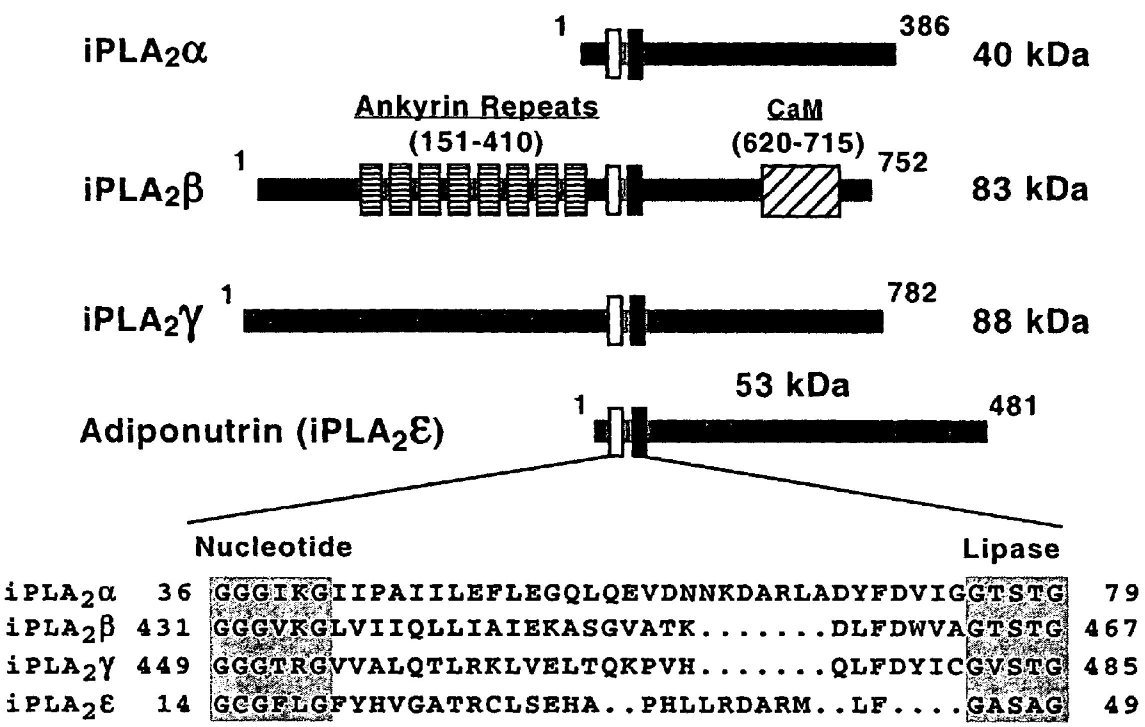
FIG. 2 shows the Calcium-Independent Phospholipase $A_2$ ($iPLA_2$) Gene Family and Sequence Alignment of $iPLA_2$ Nucleotide and Lipase Consensus Motifs. Members of the $iPLA_2$ gene family (α(SEQ ID NO: 5), β (SEQ ID NO: 6), γ (SEQ ID NO: 7), and ϵ (SEQ ID NO: 8)) are aligned according to their conserved nucleotide-binding motifs (open bars) and lipase consensus sites (filled bars).

FIG. 2 shows the Calcium-Independent Phospholipase $A_2$ ($iPLA_2$) Gene Family and Sequence Alignment of $iPLA_2$ Nucleotide and Lipase Consensus Motifs. Members of the $iPLA_2$ gene family (α, β, γ, and ϵ) are aligned according to their conserved nucleotide-binding motifs (open bars) and lipase consensus sites (filled bars). Calcium-independent phospholipase $A_2\beta$ contains eight ankyrin repeat domains (boxed horizontal bars) and a calmodulin-binding domain (CaM) near the C-terminus (boxed diagonal bars).

FIGS. 3A and 3B provide Nucleotide and Deduced Amino Acid Sequences of Our Newly Discovery Human Adiponutrin ($iPLA_{2\epsilon}$) and variants thereof. A. Glu434 Variant (refSNP ID=2294918(g); Sequence ID+AK025665 (nucleotide)) B. Lys434 Variant (refSNP ID=2294918(a); Sequence ID=AL138578.2 (nucleotide): NP_079501 (protein)). The depicted nucleotide coding sequences (lower case letters) of human adiponutrin (1446 bp) encode for polypeptides of 481 amino acids (upper case letters). The amino acid encoded for each adiponutrin ($iPLA_2\epsilon$) allelic variant is boxed. The conserved nucleotide binding (GCGFLG) (SEQ ID NO: 11) and lipase (GASAG) (SEQ ID NO: 12) consensus sequences are indicated with dashed and solid lines, respectively. The catalytic serine (Ser-47) is depicted to illustrate the native (where R=H) or acylated enzyme (where R=any fatty acyl moiety).

FIG. 3A and FIG. 3B show our novel nucleic acids and our novel enzymes claimed herein as $iPLA_2\epsilon$. SEQ ID#'s (for page 2 herein) are at the top of FIG. 3A and 3B. SEQ ID NO. 1 is FIG. 3A (listed protein sequence); SEQ ID NO. 2 is FIG. 3B (listed protein sequence); SEQ ID NO. 3 is FIG. 3A (listed nucleotide sequence); and SEQ ID NO. 4 is FIG. 3B (listed nucleotide sequence) such variants are included herein as $iPLA_2\epsilon$.

Figure 4:
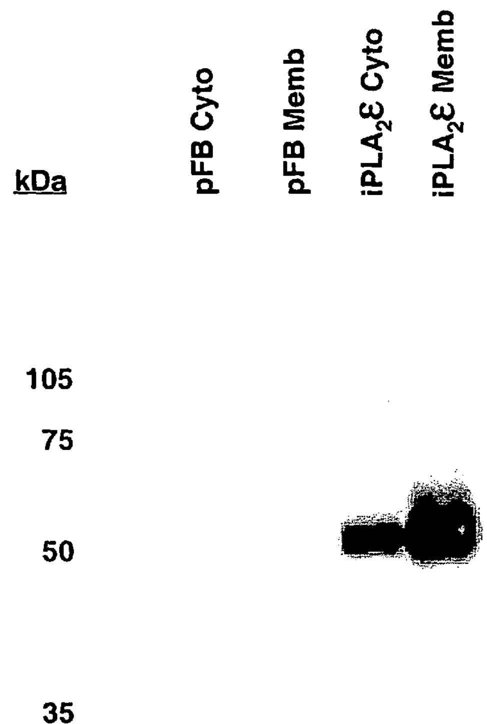
FIG. 4 shows Western Analysis of the Subcellular Localization of Recombinant Human Adiponutrin ($iPLA_{2\epsilon}(His)_6$) ($His_6$ shown as SEQ ID NO: 10).

FIG. 4 shows Western Analysis of the Subcellular Localization of Recombinant Human Adiponutrmn ($iPLA_2\epsilon(His)_6$) ($His_6$ shown as SEQ ID NO: 10). Sf9 cells infected with either control empty-vector pFastBac (pFB) or pFB encoding human adiponutrin ($iPLA_2\epsilon$) for 48 h were pelleted, washed once in ice-cold phosphate buffered saline, and resuspended in 25 mM sodium phosphate buffer, pH 7.0 containing 20% glycerol and 2 mM 2-mercaptoethanol. After lysis by sonication, cytosol (Cyto) and membrane (Memb) fractions were isolated by ultracentrifugation (100,000×g for 1 h). Proteins from the cytosol and membrane fractions were resolved by SDS-PAGE (50 μg/lane), transferred to a PVDF membrane, and probed with an antibody immunoreactive toward residues 295-310 of human adiponutrin ($iPLA_2\epsilon$). Immunoreactive bands were visualized by enhanced chemiluminescence (ECL) following incubation of the blot with a protein A-horse radish peroxidase conjugate.

Figure 5A:
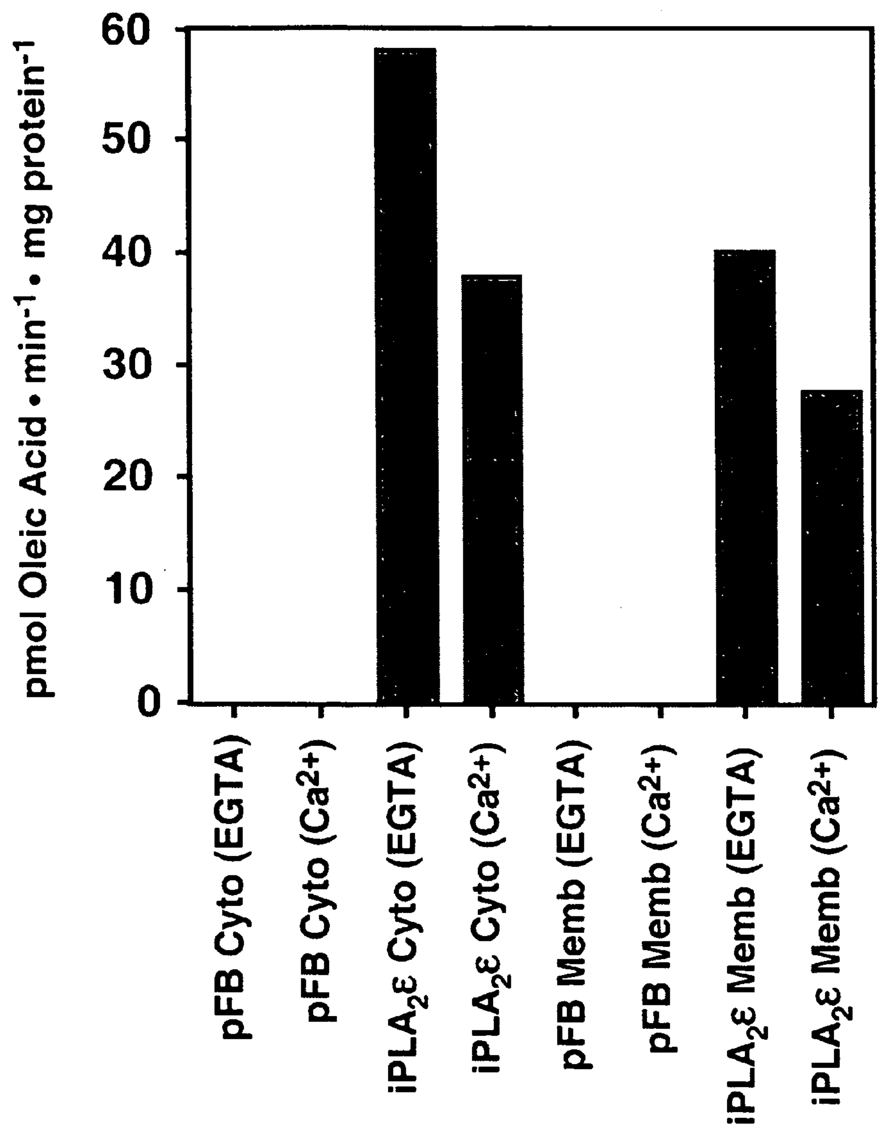
FIG. 5A shows Phospholipase $A_2$ Activity of Recombinant $iPLA_2\epsilon(His)_6$.

FIG. 5A shows Phospholipase $A_2$ Activity of Recombinant $iPLA_2\epsilon(His)_6$. Sf9 cytosol and membrane fractions were isolated from pFB control and human adiponutrin ($iPLA_2\epsilon$)-expressing cells ($iPLA_2\epsilon$) as described more particularly hereafter. Subcellular fractions were incubated with 1-palmitoyl-2-[1-$^{14}$C]-oleoyl-sn-glycero-3-phosphatidylcholine in the presence of 100 mM Tris-HCl, pH 7.5 containing either 10 mM $CaCl_2$ or 4 mM EGTA at 37° C. for 5 min. Radiolabeled product and remaining substrate were extracted into butanol, resolved by thin-layer chromatography, and quantified by scintillation spectrometry as described more particularly hereafter.

Figure 5B:
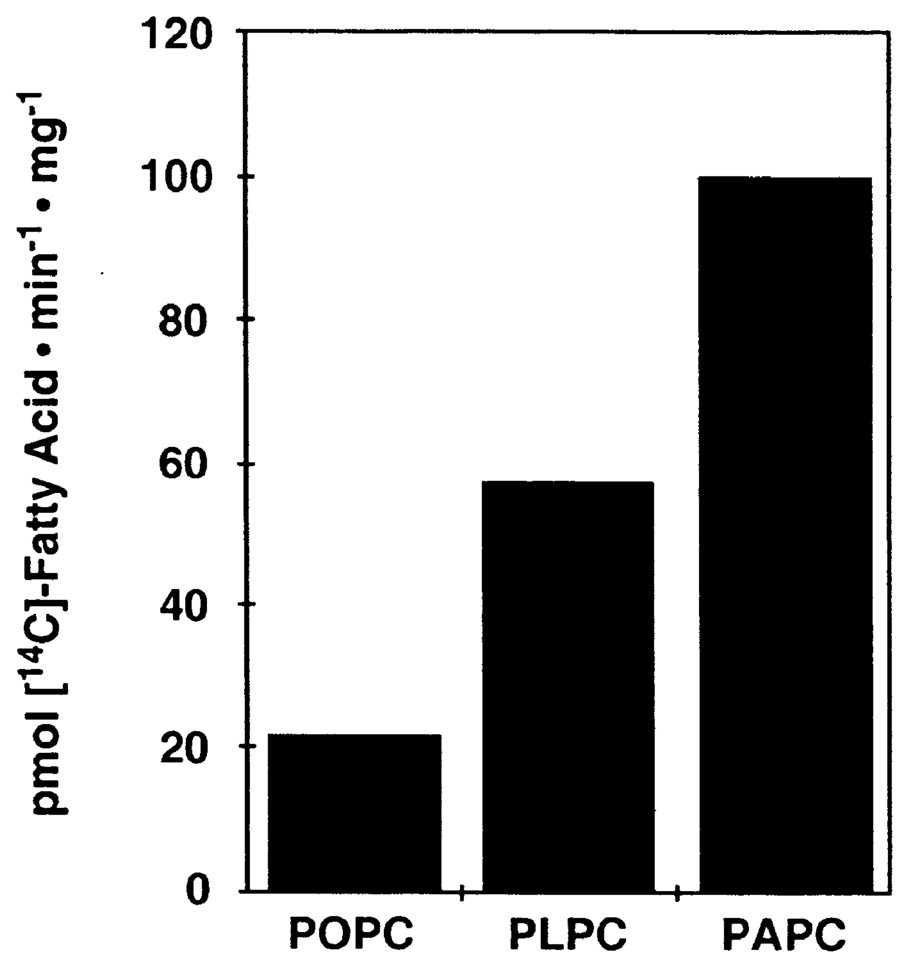
FIG. 5B shows Phospholipase $A_2$ Activity of Affinity Purified Human Adiponutrin ($iPLA_2\epsilon(His)_6$) ($His_6$ shown as SEQ ID NO: 10).

FIG. 5B shows Phospholipase $A_2$ Activity of Affinity Purified Human Adiponutrin (iPLA$_2$ε(His)$_6$) (His$_6$ shown as SEQ ID NO: 10) Affinity purified recombinant human adiponutrin (iPLA$_{2ε}$(His)$_6$) was incubated in 100 mM Tris-HCl, pH 7.2 containing 4 mM EGTA (200 μl final volume) for 30 min at 37° C. in the presence of 1-palmitoyl-2-[1-$^{14}$C]-oleoyl-sn-glycero-3-phosphocholine (POPC), 1-palmitoyl-2-[1-$^{14}$C]-linoleoyl-sn-glycero-3-phosphocholine (PLPC), or 1 -palmitoyl-2-[1-$^{14}$C]-arachidonyl-sn-glycerol-3-phosphocholine (PAPC) introduced by ethanolic injection. Reactions were terminated by addition of 100 μl of butanol and extraction of the radiolabeled product and remaining substrate into the butanol layer by vigorous vortexing. Samples were spotted on LK6 Silica Gel 60 Å TLC plates, overlaid with oleic acid standard, dried, and developed in petroleum ether/ethyl ether/acetic acid (70:30:1). The region of the plate corresponding to the oleic acid standard (visualized by iodine staining) was scraped into scintillation vials and quantified by liquid scintillation spectrometry.

Figure 5C:
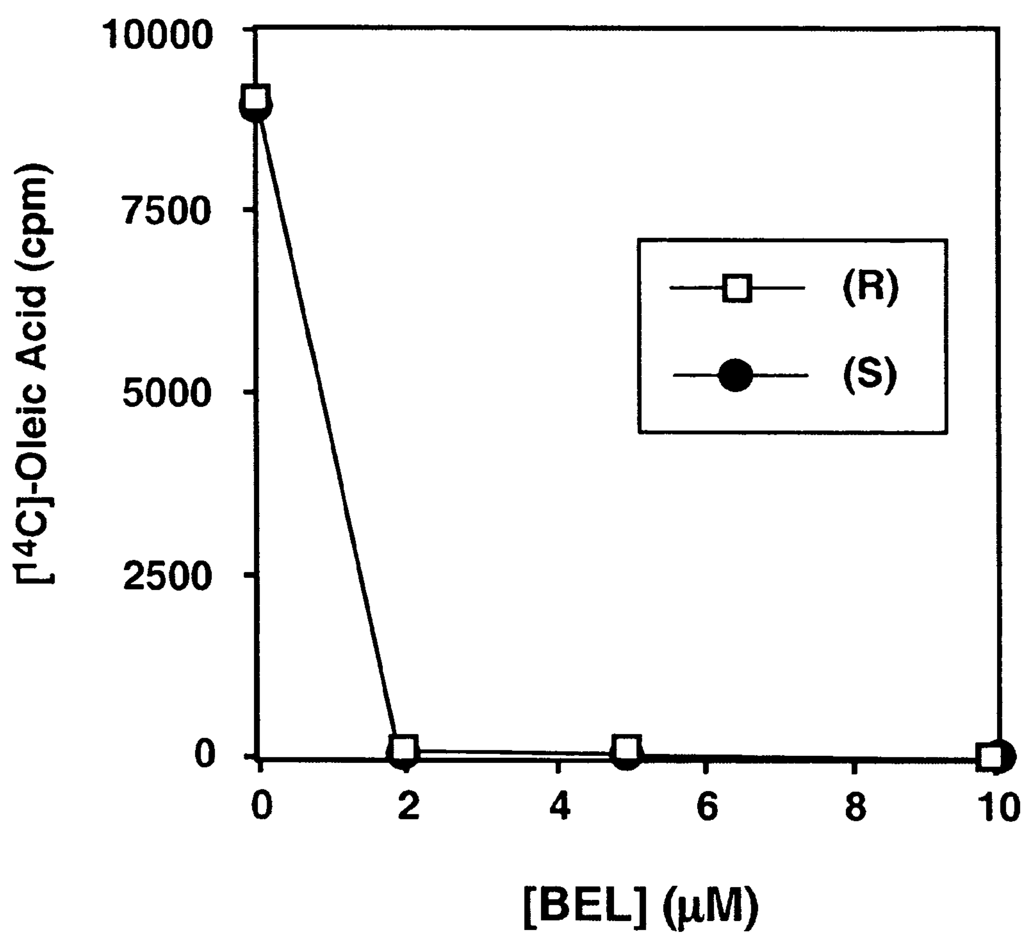
FIG. 5C shows Inhibition of Recombinant Human Adiponutrin ($iPLA_2\epsilon(His)_6$) ($His_6$ shown as SEQ ID NO: 10) Phospholipase $A_2$ Activity by (E)-6-(bromomethylene)-3-(1naphthalenyl)-2H-tetrahydropyran-2-one (BEL).

FIG. 5C shows Inhibition of Recombinant Human Adiponutrin (iPLA$_2$ε(His)$_6$) (His$_6$ shown as SEQ ID NO: 10) Phospholipase $A_2$ activity by (E)-6-(bromomethylene)-3-(1-naphthalenyl)2H-tetrahydropyran-2(BEL). Affinity purified human iPLA$_2$ε(His)$_6$ (His$_6$ shown as SEQ ID NO: 10) was pre-incubated with the indicated concentrations of (R)-BEL and (5)-BEL at 23° C. for 3 min Radiolabeled substrate (1-palmitoyl-2-[1-$^{14}$C]-oleoyl-sn-glycero-3-phosphatidyi-choline) dissolved in ethanol was then added to each reaction, mixed by vortexing, and incubated for 5 min at 37° C. Released [1-$^{14}$C]-oleic acid was quantified as described more particularly hereafter.

Figure 6A:
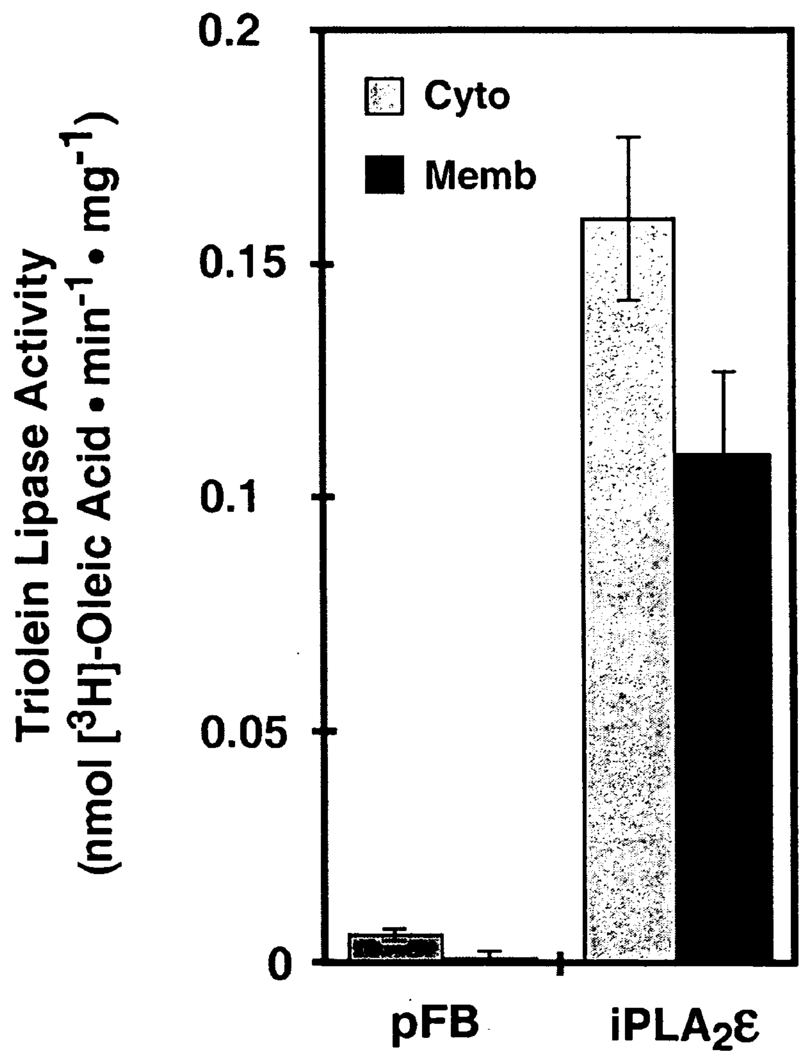
FIG. 6A shows Triolein Lipase Activity of Sf9 Subcellular Fractions Containing Recombinant Human $iPLA_2\epsilon(His)_6$ ($His_6$ shown as SEQ ID NO: 10).

FIG. 6A shows Recovered Triolein Lipase Activity of Sf9 Subcellular Fractions Containing Recombinant Human iPLA$_2$ε(His)$^6$ (His$_6$ shown as SEQ ID NO: 10). Cytosol and membrane fractions were prepared from cells infected with either control pFastBac (pFB) baculovirus or baculovirus encoding human iPLA$_2$ε(His)$_6$ (His$_6$ shown as SEQ ID NO: 10) and incubated in the presence of [9,10-$^3$H(N)]-triolein at 37° C. for 15 min as described more particularly hereafter. Radiolabeled products and unreacted substrate were extracted into butanol, separated by thin layer chromatography, and released [9,10-$^3$H]-oleic acid was quantified by scintillation spectrometry. Data presented are the averages (±S.E.) of three independent experiments performed in duplicate.

Figure 6B:
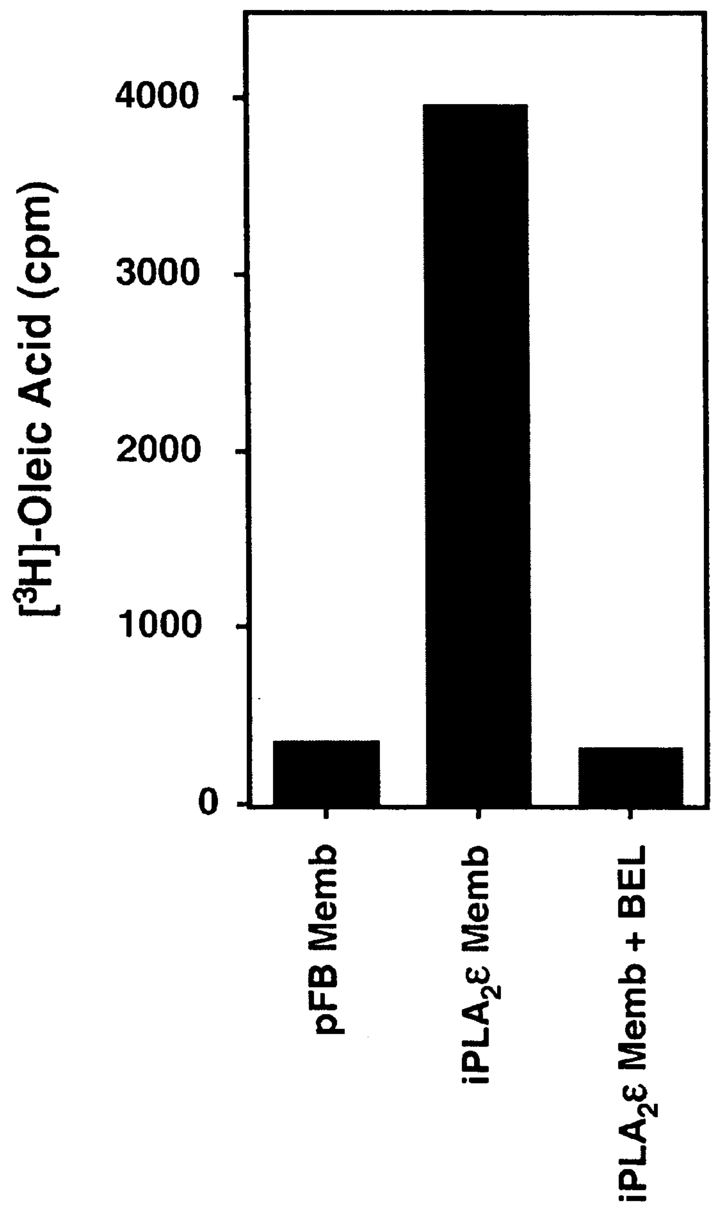
FIG. 6B shows Inhibition of Recombinant Human Adiponutrin ($iPLA_2\epsilon(His)_6$) ($His_6$ shown as SEQ ID NO: 10) Triolein Lipase Activity by BEL.

FIG. 6B shows Inhibition of Recombinant Human Adiponutrin (iPLA$_2$εHis)$_6$ (His$_6$ shown as SEQ ID NO: 10) Triolein Lipase Activity by BEL. Sf9 membranes from pFB control or human adiponutrin (iPLA$_2$ε(His)$_6$-expressing cells (iPLA$_2$ε) (His$_6$ shown as SEQ ID NO: 10) were incubated with 100 μM [9,10-$^3$H(N)]-triolein in 85 mM potassium phosphate, pH 7.0 in the presence of 25 μM lecithin and 12.5 μM sodium taurocholate in the presence or absence of 10 μM BEL. Released [9,10-$^3$H(N)]-oleic acid was extracted into butanol, resolved from remaining radiolabeled substrate and products by TLC, and quantified by scintillation spectrometry as described more particularly hereafter.

Figure 6C:
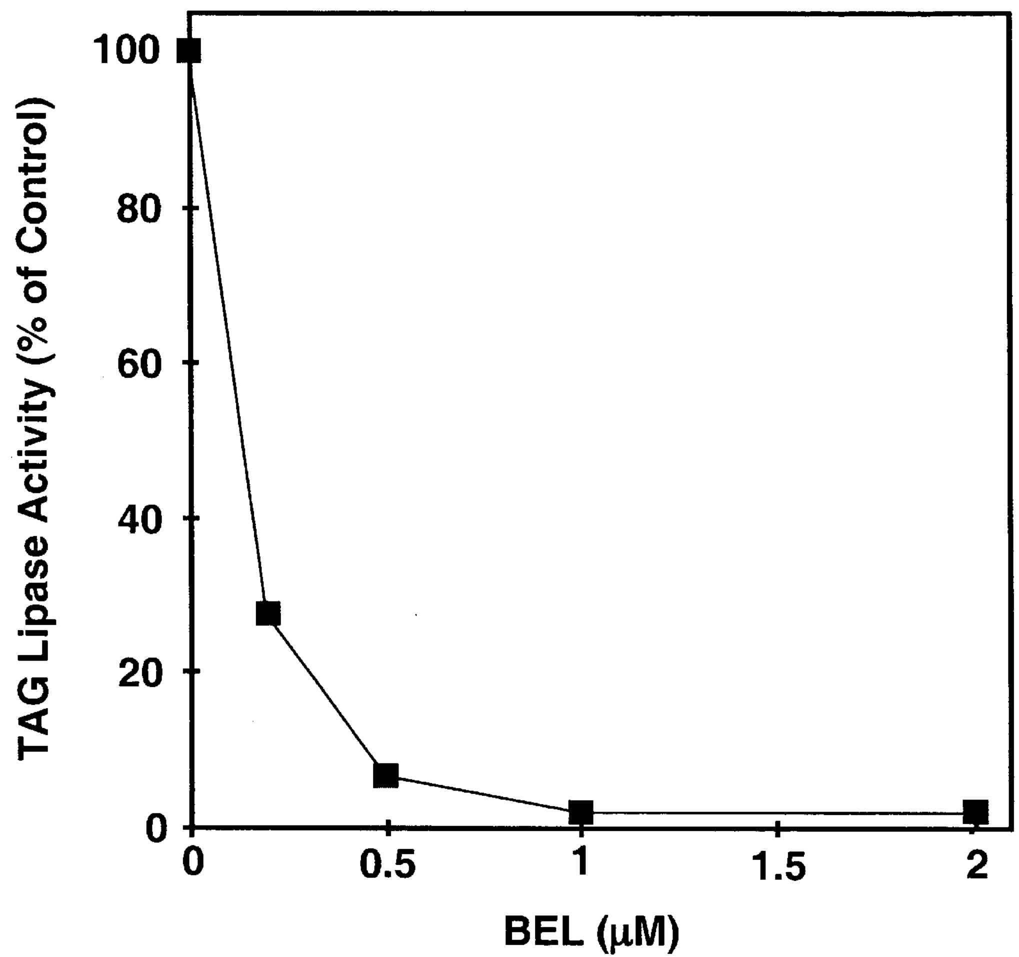
FIG. 6C shows Inhibition of Affinity Purified Recombinant Human $iPLA_2\epsilon(His)_6$ ($His_6$ shown as SEQ ID NO: 10) Triolein Lipase Activity by BEL.

FIG. 6C shows Inhibition of Recombinant Human iPLA$_2$ε(His)$_6$ (His$_6$ shown as SEQ ID NO: 10) Triolein Lipase Activity by BEL. Affinity purified iPLA$_2$ε(His)$_6$ (His$_6$ shown as SEQ ID NO: 10) was incubated with the indicated concentrations of BEL for 3 min at 23° C. Following addition of a buffered suspension of [9,10-$^3$H(N)]-triolein, samples were incubated for 15 min at 37° C. as described more particularly hereafter. Radiolabeled products and unreacted substrate were extracted into butanol, separated by thin layer chromatography, and released [9,10-$^3$H]-oleic acid was quantified by scintillation spectrometry. Data presented are the average values from four independent determinations.

Figure 7:
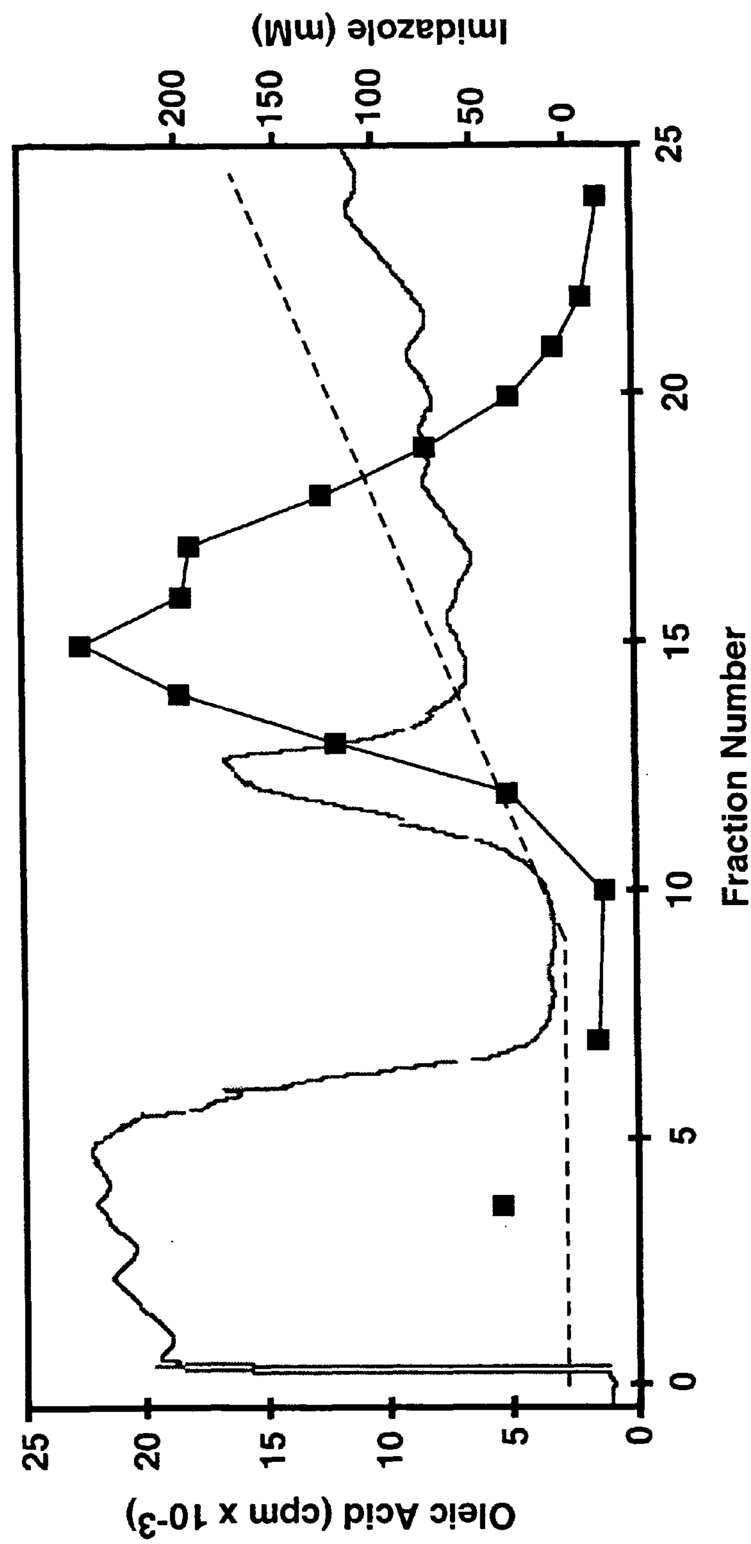
FIG. 7 shows TALON-$Co^{2+}$ Affinity Chromatography of Recovered Recombinant Human Adiponutrin ($iPLA_2\epsilon(His)_6$) ($His_6$ shown as SEQ ID NO: 10).

FIG. 7 shows TALON-Co$^{2+}$ Affinity Chromatography of Recovered Recombinant Human Adiponutrin (iPLA$_2$ε(His)$_6$) (His$_6$ shown as SEQ ID NO: 10). The cytosolic fraction (20 ml) from Sf9 cells expressing recombinant human adiponutrin (iPLA$_2$ε(His)$_6$) (His$_6$ shown as SEQ ID NO: 10) was mixed by inversion with 2.5 ml of TALON-Co$^{2+}$ affinity resin for 1 h at 4° C. The cytosol-resin suspension was poured into an empty Pharmacia column (1×10 cm) and washed with 8 column volumes of Buffer A (25 mM sodium phosphate, pH 7.8 containing 20% glycerol, 500 mM NaCl, and 2- mercaptoethanol). Bound human adiponutrin (iPLA$_2$ε(His)$_6$) (His$_6$ shown as SEQ ID NO: 10) was then eluted with a gradient of imidazole in Buffer A as indicated by the dashed line. Collected fractions were assayed for triolein lipase activity as described more particularly hereafter. The triolein lipase specific activity within peak fractions following elution of iPLA$_2$ε(His)$_6$ (His$_6$ shown as SEQ ID NO: 10) from the Co$^{2+}$-charged TALON column was 6.7±0.4 nmol of oleic acid·min$^{-1}$·mg protein$^{-1}$.

Figure 8:
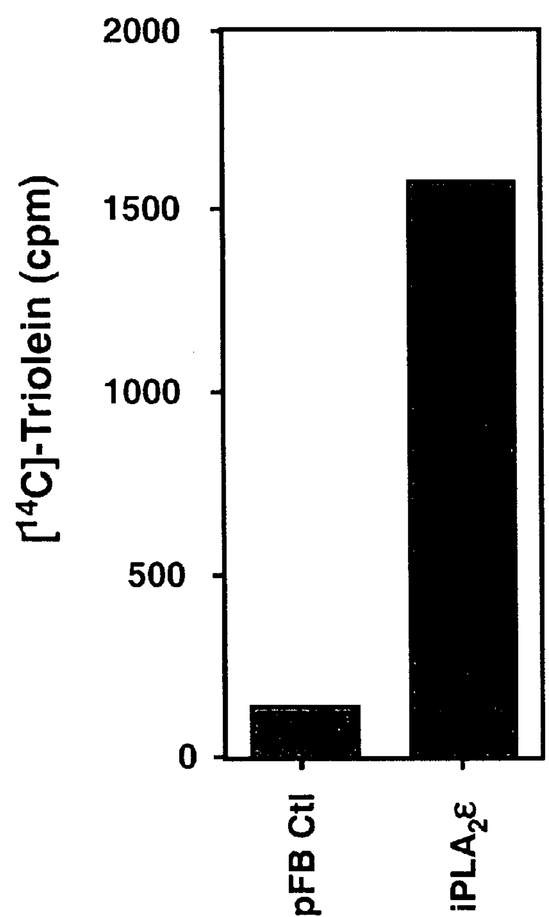
FIG. 8 shows Recombinant Human Adiponutrin ($iPLA_2\epsilon(His)_6$) ($His_6$ shown as SEQ ID NO: 10) Catalyzes Transacylation of [$^{14}$C]-Mono-olein (donor) to Mono-olein and Diolein (acceptors) to form Triolein.

FIG. 8 shows Recombinant Human Adiponutrin (iPLA$_2$ε(His)$_6$) (His$_6$ shown as SEQ ID NO: 10) Catalyzes Transacylation of [$^{14}$C]-Mono-olein (donor) to Mono-olein and Diolein (acceptors) to form Triolein. A. Sf9 cell cytosolic fractions from pFB control and human adiponutrin (iPLA$_2$ε(His)$_6$) (His$_6$ shown as SEQ ID NO: 10) (AdipoN) were incubated in 85 mM potassium phosphate buffer, pH 7.0 containing 2 mM EDTA, 1 mM DTT, 100 μM diolein (acyl acceptor), and 10 μM [oleoyl-1-$^{14}$C]-mono-olein (acyl donor) at 37° C. for 30 min. Radiolabeled products and remaining substrate were extracted into butanol, resolved by TLC, and quantified by scintillation spectrometry as described more particularly hereafter.

Figure 9:
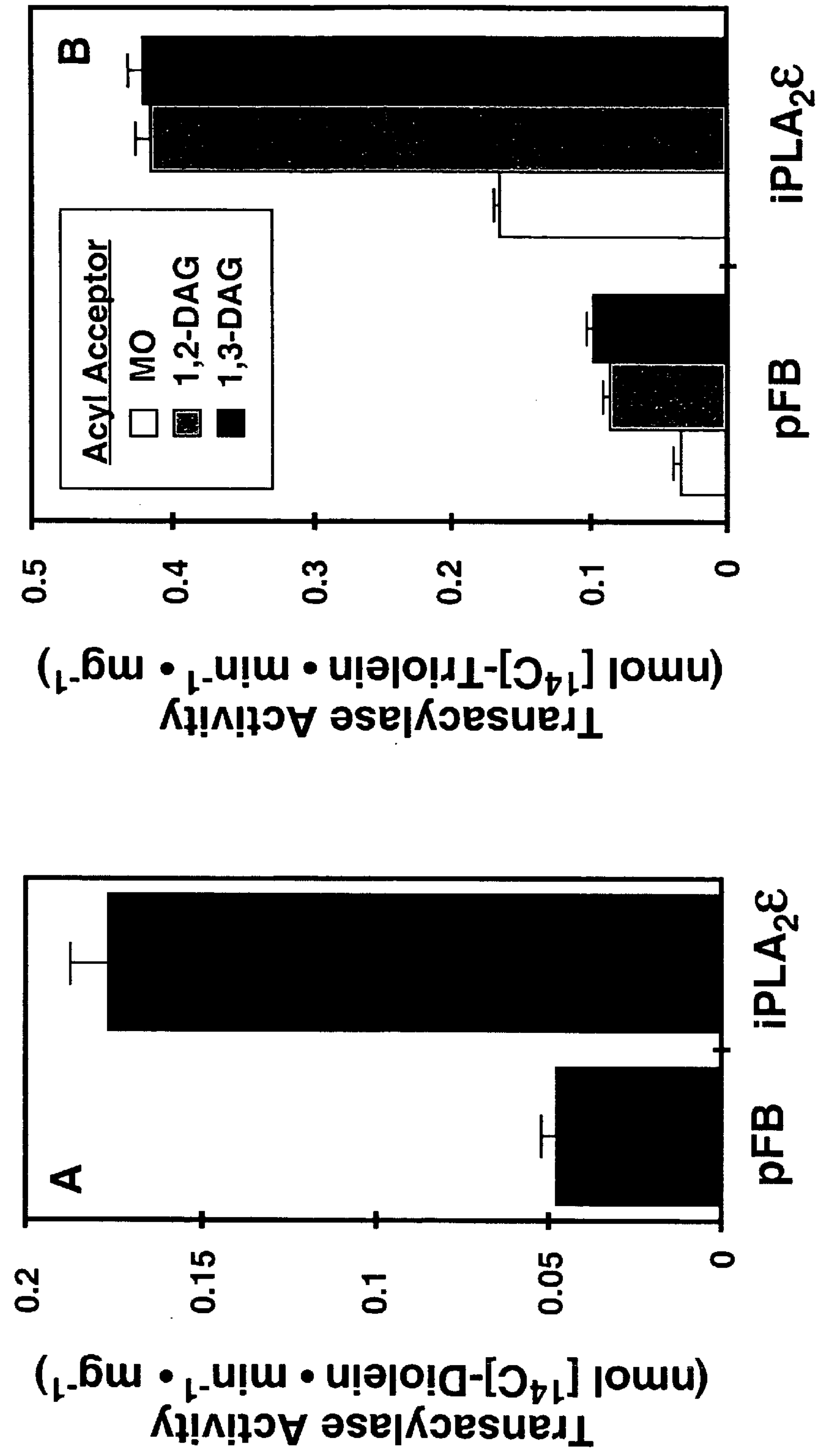
FIG. 9 shows Affinity Purified Recombinant $iPLA_2\epsilon(His)_6$ ($His_6$ shown as SEQ ID NO: 10 Catalyzes Transacylation of Mono-olein to Form Diolein and Triolein.

FIG. 9 shows Affinity Purified Human iPLA$_2$ε(His)$_6$ (His$_6$ shown as SEQ ID NO: 10) Catalyzes Transacylation of Mono-olein to Form Diolein and Triolein. A, [$^{14}$C-1]-diolein production from [$^{14}$C-1]-mono-olein. B, [$^{14}$C-1]triolein production from [$^{14}$C-1]-mono-olein. Fractions from pFB control and human iPLA$_2$ε(His)$_6$(His)$_6$shown as SEQ ID NO: 10) were incubated with [$^{14}$C-1]-mono-olein acyl donor in the presence or absence of 1,2-diolein (1,2-DOG) or 1,3-diolein (1,3-DOG) acyl acceptor at 37° C. for 15 min. Radiolabeled products and remaining substrate were extracted into butanol, resolved by TLC, and quantified by scintillation spectrometry as described more particularly hereafter. Data presented are the averages (±S.E.) of three independent experiments performed in duplicate.

Figure 10:
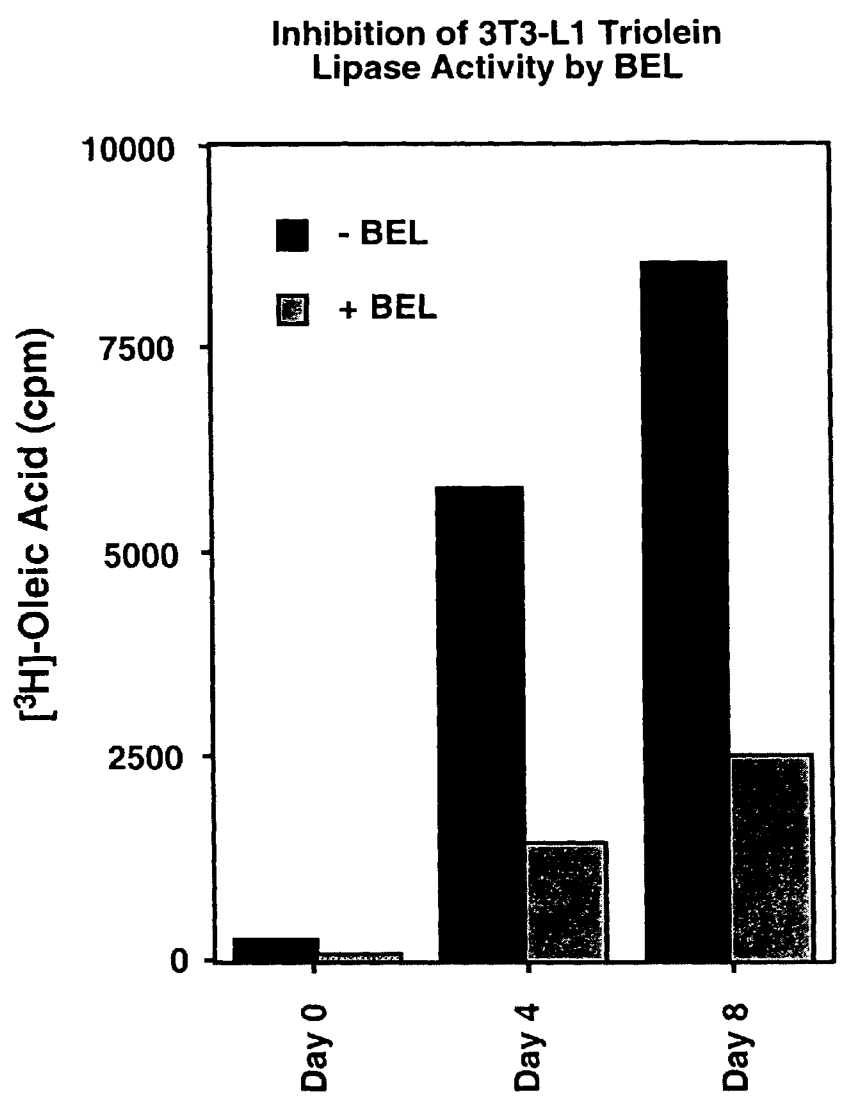
FIG. 10 shows effective and successful Inhibition of 3T3-L1 Triolein Lipase Activity by BEL.

FIG. 10 shows effective and successful Inhibition of 3T3L1 Triolein Lipase Activity by BEL. 3T3L1 adipocytes at Day zero, Day 4, and Day 8 of differentiation were harvested and lysed in 50 mM Tris-HCl, pH 7.0 containing 0.25 M sucrose, 1 mM EDTA, and 2 μg/ml leupeptin. Cell homogenates were assayed for total triolein lipase activity by incubating in 85 mM potassium phosphate, pH 7.0 containing 1 M NaCl, 25 μM lecithin, 12.5 μM sodium taurocholate, and 100 μM [9,10-$^3$H(N)]-triolein for 30 min at 37° C. Radiolabeled products ([9,10-$^3$H(N)]-oleic acid) and remaining substrate were extracted into butanol, resolved by TLC, and quantified by scintillation spectrometry as described more particularly hereafter.

Figure 11:
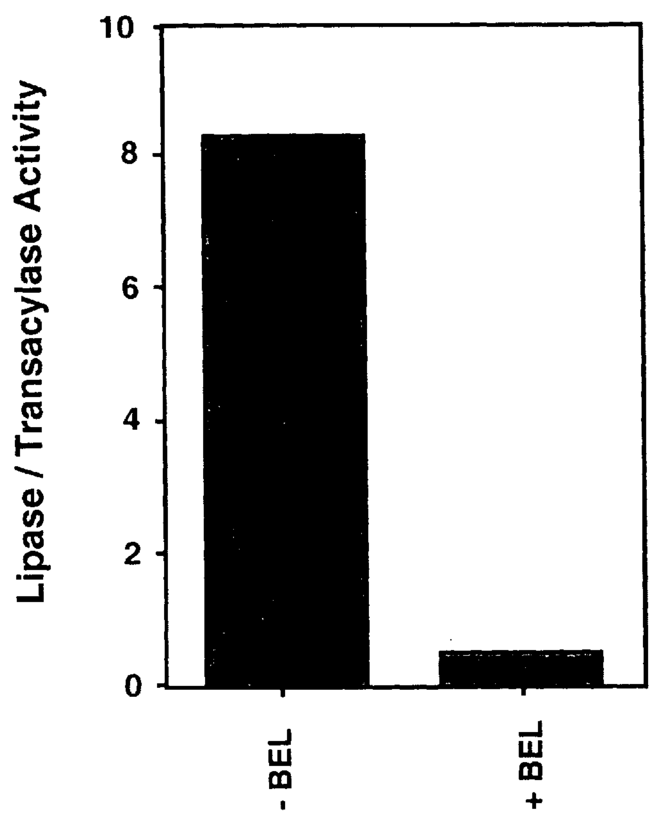
FIG. 11 shows our Modulation of Recombinant Human Adiponutrin ($iPLA_2\epsilon(His)_6$) ($His_6$ shown as SEQ ID NO: 10) Lipase/Transacylase Ratio by BEL.

FIG. 11 shows our Modulation of Recombinant Human Adiponutrin (iPLA$_2$ε(His)$_6$) (His$_6$ shown as SEQ ID NO: 10) Lipase/Transacylase Ratio by BEL Triolein lipase and transacylation (mono-olein (acyl-donor) to diolein (acyl-acceptor) to form triolein). Activities of recombinant human adiponutrin (iPLA$_2$ε(His)$_6$) (His$_6$ shown as SEQ ID NO: 10) were measured in the presence and absence of 10 mM BEL as described in Test Procedures. Addition of BEL caused marked inhibition of iPLA$_2$ε(His)$_6$) (His$_6$ shown as SEQ ID NO: 10) triolein lipase activity while having no effect on the transacylation activity of the enzyme.

FIG. 12 shows Quantitative PCR of iPLA$_2$ε Message in Mouse 3T3-L1 Preadipocytes and Human SW872 Liposarcoma Cells. Relative mouse iPLA$_2$ε (adiponutrin) mRNA levels (Panel A) in differentiating 3T3-L1 cells. Total RNA was extracted from 3T3-L1 cells on the day indicated, reverse transcribed, and the appropriate primer/probe sets were utilized to determine by quantitative PCR the relative amounts of mouse iPLA$_2$ε mRNA present as described more particularly hereafter. Data presented are representative of three independent experiments (average±S.E.). Panel B, quantitative PCR amplification curves for iPLA$_2$ε (solid circles) mRNA levels in SW872 cells. Total RNA was isolated from confluent SW872 cells, reverse transcribed, and the appropriate primer/probe sets were utilized to determine by quantitative PCR the relative amounts of human iPLA$_2$ε mRNA present as described more particularly hereafter. ΔRn indicates the change in relative fluorescence of the FAM reporter dye.

DETAILED DESCRIPTION OF THE INVENTION

The inventors have discovered (e.g. isolated and characterized) a human iPLA$_{2ε}$ gene and variants and successful and isolated and recovered and characterized expressed proteins therefrom which is involved in the hydrolysis and recycling of the hydrolysis of lipids in fat cells of the human body. In connection therewith, the inventors identified and present for the first time the specific adipocyte human protein target iPLA$_2$ε. (See FIGS. 3A and 3B)

Further, the inventors have discovered a medical treatment for combating obesity and over-weightness in humans which comprises effectively administering an effective inhibiting amount of a compound which blocks or inhibits human iPLA$_2$ε expression or enzymatic activity in a living cell. In an aspect the living cell is in a human and a determination is made after such successful administration if the patient has changed weight. If so, it is determined that the treatment was successful.

The inventors have also discovered a useful screening method and research tool for identifying drugs which are useful to successfully hold weight in a living mammal or if desired to reduce weight gain.

In an aspect, this invention is used to identify an siRNA (and its staple chemical derivatives), antisense DNA or pharmaceutical compounds modulating the activity of iPLA$_2$ε which can then be injected, applied as salve, taken orally or otherwise placed in close spatial proximity of a targeted adipose depot where it can modulate the content of fat in said tissue or total weight, appetite or insulin sensitivity of a patient and thus in essence be used for body sculpting to provide a non surgical alternative to plastic surgery or other methods of fat removal and improved appearance.

In an aspect, this invention can be used through either antisense DNA, siRNA or pharmaceutical compounds to modulate the activity of iPLA$_2$ε and thereby alternate the release of endocrine regulators from fat cells thereby altering appetite, the leptin responsive genes, adiponectin release or those of other hormones released from the fat cell in response to the fat cell's loaded state which effect its endocrine function in a way to positively modify weight control, insulin sensitivity or physical appearance.

In an aspect, a suitable sequence for siRNA suitable for silencing a gene is obtained by providing Dharmacon, Inc. 1376 Miners Drive #101 Lafayette, Colo. 80026 with a suitable sequence of a gene to be silenced. Dharmacon employs a custom proprietary process to identify candidate siRNA based on the initial gene sequence from a submitter. In an aspect, siRNA is identified by providing Dharmacon with Seq. Id. No. 3.

The construction of a suitable vector can be achieved by any of the methods well-known in the art for the insertion of exogenous DNA into a vector. see Sambrook et al., 1989, Molecular Cloning, A Laboratory Manual, Cold Spring Harbor Press, N.Y.; Rosenberg et al., Science 242:1575-1578 (1988); Wolff et al., PNAS 86:9011-9014 (1989). For Systemic administration with cationic liposomes, and administration in situ with viral vectors, see Caplen et al., Nature Med., 1:39-46 (1995); Zhu et al., Science, 261:209-211 (1993); Berkner et al., Biotechniques, 6:616-629 (1988); Trapnell et al., Advanced Drug Delivery Rev., 12:185-199 (1993); Hodgson et al., BioTechnology 13:222 (1995).

In a further aspect, transfectamine is obtained from InVitrogen Corporation, 1600 Faraday Avenue, P.O. Box 6482, Carlsbad, Calif. 92008 and/or Calgene Inc., 1920 Fifth Street, Davis, Calif. 95616 and a mixture is prepared in a tissue culture. This tissue culture is taken in tumor cells which "eat" the admixture comprising siRNA. Without being bound by theory, it is believed that siRNA is an effective toxic agent against a gene comprising a polynuclotide having a sequence shown in SEQ ID NO: 3 Technical information which provides useful tools for identifying siRNA using a sequence of a polynucleotide such as SEQ ID NO: 3 can be found on the Whitehead Biocomputing group website. This information is incorporated herein in its entirety by reference.

In an aspect, the discovery and the sequences contained herein (protein, nucleic acid, SNPs and their covalent modifications in both complete sequence and salient parts) are used as biomarkers indicative of disease states related to lipid metabolism including but not limited to the metabolic syndrome, the diagnosing and worsening of obesity, and the efficacy of drug treatment for obesity, hypertension, atherosclerosis or inflammation. It is envisaged that cardiac risk, susceptibility to stroke, renal failure and/or diabetes will be more accurately assessed based upon the type, amount and modifications of the iPLA$_2$ε sequences described herein. Accordingly, its utility as both a biomarker for atherosclerosis, diabetes, incipient hypertension or heart attacks should be available from the judicious use of serum and biopsy samples (DNA sequencing for SNPs, post translational modifications, and amount and half live of salient entities) to develop effective pharmaceuticals (including but not limited to traditional low molecular weight entities, antisense DNA and siRNA) as well as to evaluate their efficacy in treatment or identifying specific subgroups who would most greatly benefit from such treatment.

As used herein, the term "compound" includes cell(s), compounds, ions/anions, cations and salts.

As used herein, the term "adipocyte" includes any cell storing fat.

As used herein, the term "sIRNA" means functional short interfering RNA. Articles which describe the effects of small interfering RNA (siRNA) on silencing genes are 1. Elbashir, S M et al (2001) Nature, 411,494-498; 2. Hannon, G J (2002) Nature, 418, 244-251 and 3. Tijsterman, M (2002) Annu. Rev. Genet., 36, 489-519, Instruction for siRNA construction is available from Silencer™ siRNA Construction Kit Instruction Manual. Catalog #: 1630, Ambion Inc., 2130 Woodward St., Austin, Tex. 78744-1832. USA. Instruction for siRNA translecuon is available in Silencer™ siRNA Transfection Kit Instruction Manual, Catalog #: 1630, Ambion Inc., 2130 Woodward St., Austin, Tex. 78744-1832, USA. Additional information is available on Ambion's Technical Resources website at TechNotes Vol. 10:1.

The phrase "a sequence encoding a gene product" refers to a nucleic acid that contains sequence information, e.g., for a structural RNA such as rRNA, a tRNA, the primary amino acid sequence of a specific protein or peptide, a binding site for a transacting regulatory agent, an antisense RNA or a ribozyme. This phrase specifically encompasses degenerate codons (i.e., different codons which encode a single amino acid) of the native sequence or sequences which may be introduced to conform with codon preference in a specific host cell.

By "host cell" is meant a cell which contains an expression vector and supports the competent replication or expression of the expression vector. Host cells may be prokaryotic cells such as *E. coli*, or eukaryotic cells such as yeast, insect, amphibian, e.g. *Xenopus*, or mammalian cells such as HEK293, CHO, HeLa and the like.

As used herein, the term "administration" includes the effective administration which includes the application of a drug to a sample or to the body of a patient or research subject by injection, inhalation, ingestion, or any other effective means whereby the drug is presented to the target or area of intended delivery and reception of the drug. Normally after such administration the functional effects of the drug are detected as by suitable effective analytical means to determine the effect if any of the drug following its administration.

As used herein a "therapeutic amount" is an amount of a moiety such as a drug or compound which produces a desired or detectable therapeutic effect on or in a mammal administered with the moiety.

As used herein, an "expression vector" means a nucleic acid construct, generated recombinantly or synthetically, with a series of specific nucleic acid elements which permit competent transcription of a particular nucleic acid in a host cell. The expression vector can be part of a plasmid, virus, or nucleic acid fragment. Typically, the expression vector includes a nucleic acid to be transcribed operably linked to a promoter.

As used herein the term "putative" means deemed to be, supposed, reputed to be an inhibitor of the expression of iPLA$_2$ε in iPLA$_2$ε expressible tissue such as in adipose tissue of a transgenic mouse or a sample tissue thereof or a sample adequately representative thereof.

As used herein, the terms "compound" and "moiety" includes cell(s), compounds, ions/anions, cations and salts, including living cells of a life sustaining biosystem.

As used herein, the term "tissue" includes tissue, cells and collections of a multiplicity of homogenous or nearly homogenous cell lines or a sample thereof or an adequately representative sample thereof. In an aspect the tissue is a living mammalian tissue such as in a tissue culture or living mammal or in a living transgenic mouse.

As used herein, the term "peptide" is any of a group of compounds comprising two or more amino acids linked by chemical bonding between their respective carboxyl and amino groups. The term "peptide" includes peptides and proteins that are of sufficient length and composition to effect a biological response, e.g. antibody production or cytokine activity whether or not the peptide is a hapten. term "peptide" includes modified amino acids, such modifications including, but not limited to, phosphorylation, glycosylation, acylation prenylation, lipidization and methylation.

As used herein, the term "polypeptide" is any of a group of natural or synthetic polymers made up of amino acids chemically linked together such as peptides linked together. The term "polypeptide" includes peptide, translated nucleic acid and fragments thereof.

As used herein, the term "polynucleotide" includes nucleotide sequences and partial sequences, DNA, cDNA, RNA variant isoforms, splice variants, allelic variants and fragments thereof.

As used herein, the terms "protein", "polypeptide" and "peptide" are used interchangeably herein when referring to a translated nucleic acid (e.g. a gene product). The term "polypeptide" includes proteins.

As used herein, the term "isolated polypeptide" includes a polypeptide essentially and substantially free from contaminating cellular components.

As used herein, the term "isolated protein" includes a protein that is essentially free from contamination cellular components normally associated with the protein in nature.

As used herein, the term "nucleic acid" refers to oligonucleotides or polynucleotides such as deoxyribonucleic acid (DNA) and ribonucleic acid (RNA) as well as analogs of either RNA or DNA, for example made from nucleotide analogs any of which are in single or double stranded form.

As used herein, the term "patient" and subject" are synonymous and are used interchangeably herein.

As used herein, the term "expression" includes the biosynthesis of a product as an expression product from a gene such as the transcription of a structural gene into mRNA and the translation of mRNA into at least one peptide or at least one polypeptide.

As used herein, the term "mammal" includes living animals including humans and non-human animals such as murine, porcine, canine and feline.

As used herein, the term "sample" means a viable sample of biological tissue or fluid and is not limited to heart tissue. Biological samples may include representative sections of tissues.

As used herein, the term "target protein" includes an amino acid sequence expressed on a target cell such as on a tumor cell. In an aspect, the target protein is a protein having a sequence shown in SEQ. ID. No. 1 or SEQ. ID. No. 2.

As used herein, the term "antisense" means a strand of RNA whose sequence of bases is complementary to messenger RNA.

As used herein, the term "siRNA" means short interfering RNA.

The phrase "a sequence encoding a gene product" refers to a nucleic acid that contains sequence information, e.g., for a structural RNA such as rRNA, a tRNA, the primary amino acid sequence of a specific protein or peptide, a binding site for a transacting regulatory agent, an antisense RNA or a ribozyme. This phrase specifically encompasses degenerate codons (i.e., different codons which encode a single amino acid) of the native sequence or sequences which may be introduced to conform with codon preference in a specific host cell.

By "host cell" is meant a cell which contains an expression vector and supports the replication or expression of the expression vector. Host cells may be prokaryotic cells such as *E. coli*, or eukaryotic cells such as yeast, insect, amphibian, e.g. *Xenopus*, or mammalian cells such as HEK293, CHO, HeLa and the like.

As used herein a "therapeutic amount" is an amount of a moiety such as a drug or compound which produces a desired or detectable therapeutic effect on or in a mammal administered with the moiety.

The term "recombinant" when used with reference to a cell, or protein, nucleic acid, or vector, includes reference to a cell, protein, or nucleic acid, or vector, that has been modified by the introduction of a heterologous nucleic acid, the alteration of a native nucleic acid to a form not native to that cell, or that the cell is derived from a cell so modified. Thus, for example, recombinant cells express genes and proteins that are not found within the native (non-recombinant) forms of the cell or express native genes that are otherwise abnormally expressed, under expressed or not expressed at all.

An "expression vector" includes a nucleic acid construct, generated recombinantly or synthetically, with a series of specific nucleic acid elements which permit transcription of a particular nucleic acid in a host cell. The expression vector can be part of a plasmid, virus, or nucleic acid fragment. Typically, the expression vector includes a nucleic acid to be transcribed and operably linked to a promoter so that it is functional.

Herein, the inventors identified isolated, purified and characterized a novel human $iPLA_2$, termed $iPLA_2\epsilon$, which is homologous to mouse adiponutrin whose mRNA has been previously demonstrated to be strongly induced in vitro during differentiation of 3T3-L1 cells into adipocytes (1). Intriguingly mouse, adiponutrin mRNA rapidly increases when fasting mice are fed a high carbohydrate diet, rapidly decreases upon re-fasting, and is inappropriately upregulated in genetic models of obesity (1,2). However, here, for the first time, the inventors have identified and provide human adiponutrin as a triglyceride lipase/transferase and a transacylase and a phospholipase.

Herein, the inventors describe their cloning and heterologous expression of recovery of $iPLA_2\epsilon$, in Sf9 insect cells and demonstrate that the enzyme $iPLA_2\epsilon$ possesses calcium-independent phospholipase $A_2$ activity selective for arachidonic acid and abundant amounts of triolein lipase activity as well as transacylase activity.

Furthermore, the inventors demonstrate herein that the phospholipase $A_2$ and triolein lipase activities of this enzyme are inhibited by (E )-6-(bromomethylene)-3-( 1-naphthalenyl)-2H-tetrahydropyran-2-one (BEL), a mechanism-based suicide substrate inhibitor of all known $iPLA_2\epsilon$. We represent that $iPLA_2\epsilon$ represents a valuable pharmacologic target whose successful modulation reduces the incidence of obesity and the clinical manifestations of type 2 metabolic syndrome. The metabolic syndrome (syndrome X) is diagnosed by 3 or more abnormal findings using five thresholds, triglyceride level, LDL cholesterol, fasting glucose, systolic blood pressure and waist size.

The inventors here for the first time identified, isolated, recovered, purified and characterized human $iPLA_2\epsilon$ and practical uses for human $iPLA_2\epsilon$. In summary, the inventors identified the signature ATP consensus sequence (GXGXXG) and the active site seine nucleophile (GXSXG) (FIG. 2), in a human protein, termed $iPLA_2\epsilon$ which is homologous to mouse adiponutrin. In this application, the inventors describe the cloning and heterologous expression of human $iPLA_2\epsilon$ in Sf9 cells and demonstrate that the expressed recombinant enzyme possesses phospholipase $A_2$, triglyceride lipase and monoglyceride transferase activities which are inhibited by (E)-6-(bromomethylene)-3-(1-naphthalenyl)-2H-tetrahydropyran-2-one (BEL). Moreover, the inventors describe how human adiponutrin $iPLA_2\epsilon$ can catalyze anabolic fat synthesis by transesterification as shown in FIG. 1.

These results demonstrate that the affinity-purified $iPLA_2\epsilon$ can selectively hydrolyze polyunsaturated fatty acids at the sn-2 position which have previously been shown to be substrates for oxidative enzymes in signaling cascades. Accordingly, $iPLA_2\epsilon$ may serve to generate lipid $2^{nd}$ messengers of signal transduction.

Exemplary embodiments are described in the following examples. It is intended that the specification, together with the examples, be considered exemplary only.

EXAMPLES

Test Procedures and Results

The inventors' successful cloning of Human Adiponutrin ($iPLA_2\epsilon$)-PCR primers (5'-AAAGAATTCCACCATGTACGACGCAGAGCGCGG-CTGGAGCTT-3'(SEQ ID NO: 13) and 5'-AAAAGTCGACTCAGTGATGGTGATGGTGATGCAG-ACTCTTCTCTAGTGAA-3') (SEQ ID NO: 14) designed to introduce a C-terminal 6× His tag at the 3' end of human adiponutrin coding sequence and to incorporate 5'-EcoRI and 3'-SalI restriction sites for subcloning into the baculoviral expression vector pFASTBac1. Full-length 1.4 kb human adiponutrin was amplified from ATCC IMAGE clone ID 4870514. After sequencing the insert and flanking sequences on both strands of the adiponutrin-pFASTBac1 construct to ensure the sequence integrity of the construct, a bacmid construct was prepared using the Bac-to-Bac Baculovirus Expression System protocol (Invitrogen) for subsequent Celifectin-mediated transfection of Sf9 cells in 35 mm plates to produce infectious recombinant baculovirus. Amplified recombinant baculovirus was then used to infect a spinner culture of Sf9 cells for 72 h and the supernatant was collected as a high titer viral stock.

The inventors' successful expression of Human $iPLA_2\epsilon$ $(His)_6$ ($His_6$ shown as SEQ ID NO: 10) in Sf9 cells and Subcellular Fractionation-Sf9 cells at a density of approximately $1\times10^6$ cells/ml were infected with either control baculovirus or recombinant baculovirus encoding human $iPLA_2\epsilon$ $(His)_6$ ($His_6$ shown as SEQ ID NO: 10) or at an multiplicity of infection of approximately 1. Forty-eight hours post-infection, cells were harvested by centrifugation (250×g for 10 min), washed once in ice-cold phosphate buffered saline, re-pelleted, and resuspended in lysis buffer (25 mM sodium phosphate, pH 7.8 containing 20% glycerol and 2 mM 2-mercaptoethanol). Cells were lysed by sonication (30×s bursts at 40% power) and centrifuged at 100,000×g for 1 h to separate cytosolic and membrane fractions. Cellular membranes were resuspended in a volume of lysis buffer equivalent to the volume of the cytosol fraction.

TALON-$Co^{2+}$ Affinity Column Chromatography of our $iPLA_2\epsilon(His)_6$ ($His_6$ shown as SEQ ID NO: 10) The cytosolic fraction containing recombinant human $iPLA_2\epsilon(His)_6$ ($His_6$ shown as SEQ ID NO: 10) was mixed by inversion with 10% volume of TALON-$Co^{2+}$ resin for 1 h at 40° C. The resin-cytosol suspension was then poured into a column (1.5×10 cm) and washed with 4 column volumes of lysis buffer containing 500 mM NaCl (Buffer A). Recombinant $iPLA_2\epsilon$ $(His)_6$ ($His_6$ shown as SEQ ID NO: 10) was eluted from the column utilizing a gradient of imidazole (250 mM) in Buffer A. Fractions were collected and assayed for phospholipase $A_2$ activity as described below.

Generation and Immunoaffinity successful Purification and recovery of Anti-Human $iPLA_2\epsilon$ Antibodies—A peptide corresponding to residues 295-310 of human iPLA$_2$ε(CRLEGDELLDHLRLSIL) (SEQ ID NO: 9) was coupled to maleimide-activated mariculture keyhole limpet hemocyanin according to the instructions of the manufacturer, emulsified with Freund's complete adjuvant, and injected subcutaneouly into New Zealand white rabbits. At two week intervals, the rabbits were boosted with the peptide-KLFI conjugate emulsified in Freund's incomplete adjuvant until seroconversion occurred. The iPLA$_2$ε peptide was coupled to activated thiol-Sepharose 4B for immunoaffinity purification of the anti-peptide antibodies. Immunoreactive rabbit antisera were diluted 1:10 with 10 mM Tris-HCl, pH 7.5, prior to application to the peptide affinity column equilibrated with the same buffer. The resin was extensively washed with 10 column volumes of 10 mM Tris-HCl, pH 7.5 containing 500 mM NaCl prior to elution of bound antibodies with 0.1 M glycine-HCl, pH 1.0, into collection tubes containing 1 M Tris-HCl, pH 9.0 (1:3 fraction volume). Antibodies were concentrated, dialyzed against phosphate-buffered saline containing 20% glycerol and stored at −80° C. prior to use.

Assay for Phospholipase A$_2$ Activity—Sample fractions were incubated in 100 mM Tris-HCl, pH 7.2 containing either 4 mM EGTA or 10 mM CaCl$_2$ (200 µl final volume) for 5-30 min at 37° C. in the presence of 1-palmitoyl-2-[1-$^{14}$C]-oleoyl-sn-glycero-3-phosphatidylcholine, 1-palmitoyl-2-[1-$^{14}$C]-linoleoyl-sn-glycero-3-phosphocholine, or 1-palmitoyl-2-[1-$^{14}$C]-arachidonyl-sn-glycerol-3-phosphocholine introduced by ethanolic injection. In some reactions, BEL at the indicated concentrations was added prior to the addition of radiolabeled substrate. Reactions were terminated by addition of 100 µl of butanol and extraction of the radiolabeled product and remaining substrate into the butanol layer by vigorous vortexing. Samples were spotted on LK6 Silica Gel 60 Å TLC plates, overlaid with oleic acid standard, dried, and developed in petroleum ether/ethyl ether/acetic acid (70:30:1). The region of the plate corresponding to the oleic acid standard (visualized by iodine staining) was scraped into scintillation vials and quantified by liquid scintillation spectrometry.

Assay for Triolein Lipase Activity—Sample fractions were incubated in 85 mM potassium phosphate, pH 7.0 containing 1 M NaCl (250 µl final volume) for 30 min at 37° C. in the presence of a suspension of 100 µM [9,10-$^3$H(N)]-triolein, 25 µM egg yolk lecithin, and 12.5 µM to 100 µM sodium taurocholate. In some reactions, BEL (10 µM final concentration) was added prior to the addition of radiolabeled substrate. After extraction of radiolabeled reaction product and remaining substrate into butanol, samples were spotted on TLC plates, overlaid with oleic acid standard, dried, and developed in chloroform/methanol/$NH_4OH$ (65:25:5). The region of the plate corresponding to the oleic acid standard (visualized by iodine staining) was scraped into scintillation vials and quantified by liquid scintillation spectrometry.

Assay for lipid Transacylase Activity—Highly purified $Co^{2+}$-TALON affinity chromatographie fractions containing adiponutrin (iPLA$_{2ε}$(His)$_6$) (His$_6$ shown as SEQ NO: 10) (50 µl) were incubated in 85 mM potassium phosphate, pH 7.0 (250 µl final volume) for 15-30 min at 37° C. in the presence of a suspension of 10 µM [1-$^{14}$C]-mono-olein (acyl donor), 25 µM to 100 µM acyl-acceptor (mono-olein or diolein), 25 µM egg yolk lecithin, and 12.5 µM to 25 µM sodium taurocholate. In some reactions, BEL (10 µM final concentration) was added prior to the addition of radiolabeled substrate. After extraction of radiolabeled reaction product and remaining substrate into butanol. samples were spotted on TLC plates. overlaid with oleic acid standard, dried, and developed in petroleum ether/ethyl ether/acetic acid (70:30:1). The region of the plate corresponding to diolein or triolein standard (visualized by iodine staining) was scraped into scintillation vials and quantified by liquid scintillation spectrometry.

Quantitative PCR of iPLA$_{2ε}$ Message in Differentiating 3T3-L1 Adipocytes and SW872 Human Liposacroma Cells. 3T3-L1 pre-adipocytes were cultured and differentiated as described previously (3). Human SW872 liposarcoma cells were cultured as described previously (4). 3T3-L1 cells at day 0 through day 6 of differentiation (2 day intervals) or SW872 cells were washed twice with ice-cold phosphate buffered saline and RNA was prepared following the RNeasy (Qiagen) protocol as described by the manufacturer. RNA (0.1 -2 µkg) was reverse transcribed using MultiScribe reverse transcriptase (TaqMan Gold RT-PCR kit, Applied Biosystems) by incubation for 10 min at 25° C. followed by 30 min at 48° C. and a final step of 5 min at 95° C. 20 ng of the resultant cDNA was used for each quantitative polymerase chain reaction. Primer/probe sets for quantitative PCR were designed using Primer Express software from PE Biosystems. Probes were 5' labeled with reporter dye FAM (6-carboxylfluorescein), and 3'labeled with quenching dye, TAMRA (6-carboxytetramethylrhodamine). Human iPLA$_{2ε}$ forward (5'-GGCAAAATAGGCATCTCTCTT-ACC-3') (SEQ ID NO: 15) and reverse (5'-GGAGGGATAAGGCCACTGTAGA-3') (SEQ ID NO: 16) primers were paired with probe (5-AACATACCAAGGCATCCACGACTTCGCTC-3') (SEQ ID NO: 17). Mouse iPLA$_{2ε}$ forward (5'-ACTGCACGCGGTCACCTT-3') (SEQ ID NO): 18) and reverse (5'-CACGAGGTCCATGAGGATCTC-3') (SEQ ID NO: 19) primers were paired with probe (5-TGTGCAGTCT-CCCTCTCGGCCGTATAAT-3') (SEQ ID NO: 20). Quantitative PCR was carried out using TaqMan PCR reagents (Applied Biosystems) as recommended by the manufacturer with GAPDH primers and probe as an internal standard. Each PCR amplification was performed in triplicate for 2 min at 50° C., 10 min at 95° C., followed by 40 cycles of 15 s at 95° C. and 1 min at 60° C.

For SDS-PAGE, proteins were separated according to the method of Laemmli (5). For Western analyses, the separated proteins in SDS-PAGE gels were transferred to polyvinylidene difluoride membranes and subsequently probed with antibodies directed against the iPLA$_2$ε peptide in conjunction with a protein A-horseradish peroxidase conjugate. Protein concentrations were determined by the Coomassie Plus Protein Assay (Pierce) using BSA as standard.

To confirm our discovery that the observed sequence homology correctly identified a novel iPLA$_2$ gene, we cloned human adiponutrin (iPLA$_2$ε) (See FIGS. 3A and 3B) and heterologously expressed the C-terminal His$_6$-tagged protein (His$_6$ shown as SEQ ID NO: 10 ) in Sf9 cells. Expression of the human ortholog of adiponutrin in Sf9 cells resulted in the production of the anticipated 53 kDa protein that was predominantly present in the membrane-associated fraction as detected by Western analysis (FIG. 4). Measurement of phospholipase A$_2$ activity demonstrated that Sf9 cells expressing iPLA$_2$ε(His)$_6$(His$_6$ shown as SEQ ID NO: 10) exhibited greater PLA$_2$ activity with 1-palmitoyl-2-[1-$^{14}$C]-oleoyl-sn-glycero-3-phosphatidylcholine as substrate in comparison to wild type cells (FIG. 5A). Furthermore, human iPLA$_2$ε(His)$_6$ (His$_6$ shown as SEQ ID NO: 10), like other members of the iPLA$_2$ε family of enzymes, did not require calcium ion for activity (FIG. 5A). Following purification by TALON-$Co^{2+}$ affinity chromatography, human iPLA$_2$ε(His)$_6$ (His$_6$ shown as SEQ ID NO: 10) was demonstrated to preferentially hydrolyze polyunsaturated acyl chains (linoleoyl and arachidonyl) at the sn-2 position of choline phospholipids (FIG. 5B). Inclusion of either enantiomer ((R) or (S)) of the mechanism-based suicide substrate BEL inhibited iPLA$_2\epsilon$(His)$_6$ (His$_6$ shown as SEQ ID NO: 10) calcium-independent phospholipase activity with an $IC_{50}$ of approximately 1 μM (FIG. 5C).

Considering the ability of iPLA$_2\epsilon$(His)$_6$ (His$_6$ shown as SEQ ID NO: 10) to catalyze phosphatidylcholine hydrolysis and its specific expression in adipocytes (4), the inventors were interested to determine if iPLA$_2\epsilon$ could also catalyze the hydrolysis of triglycerides. Importantly, Sf9 cell cytosol and membranes containing recombinant human iPLA$_2\epsilon$(His)$_6$ (His$_6$ shown as SEQ ID NO: 10), reproducibly exhibited approximately 10-fold higher triolein lipase activity relative to control (pFB) cytosol and membrane fractions (FIG. 6A). Furthermore, the triglyceride lipase activity of iPLA$_2\epsilon$(His)$_6$ (His$_6$ shown as SEQ ID NO: 10) was completely inhibited by inclusion of 10 μMBEL (FIG. 6B). The $IC_{50}$ of the affinity purified human iPLA$_2\epsilon$(His)$_6$ (His$_6$ shown as SEQ ID NO: 10) for inhibition of triglyceride lipase activity was determined to be ~0.1 μM (FIG. 6C). The expressed His-tagged adiponutrin bound to a metal chelating affinity column and triglyceride lipase activity and adiponutrin mass could be eluted with imidazole (FIG. 7).

To further substantiate the importance of adiponutrin (iPLA$_2\epsilon$) in adipocyte lipid metabolism and cycling, the inventors demonstrated that recombinant human adiponutrin (iPLA$_2\epsilon$(His)$_6$) (His$_6$ shown as SEQ ID NO: 10) could catalyze triolein (triglyceride) synthesis from mono-olein and/or diolein through a transacylation reaction or sequential transacylation. Incubation of Sf9 cell cytosol containing recombinant human adiponutrin (iPLA$_2\epsilon$(His)$_6$) (His$_6$ shown as SEQ ID NO: 10) in the presence of [Oleoyl-1-$^{14}$C]-mono-olein (acyl donor and acceptor) demonstrated synthesis of [$^{14}$C]-triolein approximately 10-fold higher than that observed in control pFB reactions (FIG. 8). Following purification utilizing a TALON-$Co^{2+}$ affinity column, recombinant human adiponutrin (iPLA$_2\epsilon$(His)$_6$) (His$_6$ shown as SEQ ID NO: 10) was further demonstrated to catalyze [$^{14}$C]-diolein (TAG Intermediate) synthesis from [Oleoyl-1-$^{14}$C]-mono-olein (acyl donor and acceptor) (FIG. 9A) and [$^{14}$C]-triolein synthesis from [Oleoyl-1-$^{14}$C]-mono-olien (acyl donor) and diolein (acyl acceptor) (FIG. 9B). Thus, the inventors discovered that human adiponutrin (iPLA$_2\epsilon$(His)$_6$) (His$_6$ shown as SEQ ID NO: 10) is able to transfer acyl equivalents from mono-olein to either mono-olein or diolein acceptors resulting in net synthesis of diolein and triolein, respectively.

Upon differentiation, 3T3-L1 adipocytes (day 4 and day 8 after initiation of differentiation) express high levels of triglyceride lipase activity which is virtually at very, very low levels in undifferentiated cells (day 0). Since human adiponutrin (iPLA$_2\epsilon$) possesses TAG lipase activity which is BEL-inhibitable, the inventors were interested to determine the ability of BEL to inhibit the TAG lipase activity present in differentiated 3T3-L1 adipocytes. As shown in FIG. 10, approximately 70% of the triolein lipase activity in homogenates of day 4 and day 8 3T3-L1 cells was inhibited by BEL, suggesting that adiponutrin (iPLA$_2\epsilon$) or lipases similar to adiponutrin are expressed during differentiated 3T3-L1 cells into adipocytes.

Comparison of the sensitivity of the lipase and transacylase activities of recombinant highly purified human adiponutrin (iPLA$_{2\epsilon}$(His)$_6$) (His$_6$ shown as SEQ ID NO: 10) to inhibition by BEL revealed that the triolein hydrolase activity of human adiponutrin is at least 10-fold more sensitive to BEL inhibition than is the transacylase activity (FIG. 11). Importantly, our discovery of this result demonstrates that the distinct catalytic activities (lipase and transacylase) of human adiponutrin can be independently modulated by a pharmacologic manipulation. To this end, pharmaceutical compounds which modulate the transacylase to lipase ratio of iPLA$_{2\epsilon}$ arc an important pharmaceutical target.

To further examine the roles of iPLA$_2\epsilon$ in adipocyte biology, we determined iPLA$_2\epsilon$ mRNA levels of each isoform in both human SW872 liposarcoma cells and differentiating 3T3-L1 adipocytes. Previous Northern analyses have demonstrated the dramatic upregulation of adiponutrin (iPLA$_2\epsilon$) mRNA during 3T3-L1 adipocyte differentiation (1). Quantitative PCR utilizing primers for mouse iPLA$_2\epsilon$ revealed a marked increase in message by day 6 (FIG. 12A). Human SW872 liposarcoma cells have been previously utilized in the study of lipoprotein receptor-mediated cholesterol homeostasis. Quantitative PCR utilizing primers for iPLA$_2\epsilon$ demonstrated high levels of expression for this iPLA$_2$ isoform in SW872 cells (FIG. 12B).

Discussion

Mouse adiponutrin was first identified by others by differential hybridization as a mRNA species that was strongly induced during differentiation of 3T3 cells into adipocytes (1). Subsequent studies have shown mouse adiponutrin is an adipocyte specific protein whose mRNA is rapidly increased after feeding, vanishes quickly after fasting and is inappropriately upregulated in genetic models of obesity (1,2,6). It is also a downstream target of the thiazolidinediones (7).

In studies of hormone-sensitive lipase knockout mice, it has become apparent that other intracellular lipases exist in adipose since HSL K/O accumulated DAG identifying HSL as predominantly a DAG lipase activity (8). Evidence from multiple laboratories indicate that additional enzymes are important in adipocytes (9-11). However, the molecular identification of these other intracellular triglyceride lipases have thus far remained elusive until this discovery.

During fasting, fatty acids released from white adipose tissue undergo considerable re-esterification (recycling) into triglyceride pools (12). The fat cell specific expression of adiponutrin in conjunction with its temporarily coordinated responses to feeding and fasting in conjunction with the biochemical discovery presented herein make it likely that adiponutrin is the critical regulator of TAG hydrolysis and recycling by transacylation in the adipocyte.

In recent years fortunately a large number of combinatorial and other enhanced chemistry techniques have been developed which fortunately now allow large multimillion compound libraries of diverse compounds to be rapidly synthesized. Such techniques have the potential to greatly accelerate the discovery of compounds which have biologically useful therapeutic properties by providing large assemblies or collections of such diverse chemical compounds for biological screening. The capability to produce such large numbers of compounds for screening is a driver for new methods of screening which are not adversely effected by time and resource constraints. This produces a need for new screening methods and models to permit rapid screening of vast compound libraries.

The inventors' results unambiguously demonstrate that adiponutrin catalyzes the hydrolysis of lipids and this identifies the inventor's discovery of a method to screen for inhibitors of its enzymic activity thereby providing a new method and valuable research tool for identification of pharmaceutical agents that promote weight loss and/or decrease insulin requirements (i.e., increasing insulin sensitivity).

In this regard, (prophetic example) a transgenic animal model is prepared which is useful in such screening. In an aspect, the transgenic animal tissue model comprises a cellular entity having a vector providing a gene capably expressing human iPLA$_2\epsilon$ and the model is characterized as to at least one of weight, diet and serum fat analysis. The transgenic animal model representing a genetic model of obesity is fed a first predetermined diet and then a second predetermined diet comprising a compound selected from a library of available candidate compounds which are putative for weight reduction effect in a living mammal. After a predetermined interval of time and after consuming the diet comprising the compound, the animal model is weighed and a comparison is made between the weight of the animal model being maintained on the predetermined diet having the supplemental compound and the animal model being on a predetermined diet absent the compound. If the weight of the animal model is significantly lower for the model having received the diet containing the compound, then the determination is made that it is likely that the compound is a candidate weight reduction agent. The inference therefrom is that the compound functions as an inhibitor to the expression of $iPLA_2\epsilon$, its adipocyte protein target, allowing that determination to be made.

A noninvasive method of using products of a gene comprising a polynucleotide having a sequence shown in Seq. Id. No. 3 as an indicator of the effectiveness of administered candidate drug to a living mammal having competently integrated in its genome that gene, which comprises administering the candidate drug therapy to the mammal, obtaining a sample of the animal and analyzing the sample for the extent of presence of a $iPLA_2\epsilon$, determining the extent that administration had on the mammal, thereby evaluating the effectiveness of the candidate drug, making a prioritization of the development of the drug based on that effectiveness. In an aspect prioritization includes ranking the drug as to its potential therapeutic capability as to treating obesity, reducing insulin dependence, increasing insulin sensitivity. In an aspect the mammal is a transgenic nonhuman mammal carrying the $iPLA_2\epsilon$ gene. Those of skill in the art will be aware of the known methods of competently integrating $iPLA_2\epsilon$ into the human genome.

In an aspect, a drug identified herein as an anti-obesity agent is effectively pharmacologically administered to a patient by any competent administrative means. In an aspect, a pharmacological effective amount would be delivered to the patient to provide or produce a desired lowering of fat content. In an aspect, an injection via a needle is employed to deliver an effective amount to a patient.

Following successful treatment, it may be desirable to have the patient undergo maintenance therapy to prevent the recurrence of the disease state, wherein the oligomer is administered in maintenance doses, ranging from 0.01 μg to 100 g per kg of body weight, once or more daily, to once every several years.

The specific mammalian dose is calculated according to the approximate body weight or body surface area of the patient or the volume of body space to be occupied. The dose will also be calculated dependent upon the particular route of administration selected. Further refinement of the calculations necessary to determine the appropriate dosage for treatment is routinely made by those of ordinary skill in the art. The amount of the composition actually administered will be determined by a practitioner, in the light of the relevant circumstances including the condition or conditions to be treated, the choice of composition to be administered, the age, weight, and response of the individual patient, the severity of the patient's symptoms, and the chosen route of administration.

The pharmaceutical compositions of the present invention may be effectively and successfully administered in a number of ways to mammals depending upon whether local or systemic treatment is desired and upon the area to be treated. Administration may be topical (including ophthalmic, vaginal, rectal, intranasal, transdermal), oral or parenteral. Parenteral administration includes intravenous drip, subcutaneous, intraperitoneal or intramuscular injection, or intrathecal or intraventricular administration.

Useful formulations for topical administration may include transdermal patches, ointments, lotions, creams, gels, drops, suppositories, sprays, liquids and powders. Conventional pharmaceutical carriers, aqueous, powder or oily bases, thickeners and the like may be necessary or desirable. Coated condoms, gloves and the like may also be useful.

Useful compositions for oral administration include powders or granules, suspensions or solutions in water or non-aqueous media, capsules, sachets or tablets. Thickeners, flavoring agents, diluents, emulsifiers, dispersing aids or binders may be desirable.

Useful compositions for intrathecal or intraventricular administration may include sterile aqueous solutions which may also contain buffers, diluents and other suitable additives.

Useful formulations for parenteral administration may include sterile aqueous solutions which may also contain buffers, diluents and other suitable additives.

In an aspect this type of screening may be done on a nontransgenic or normal (wild) type species of life.

In an aspect, the invention further comprises a method to measure and determine the metabolic effects if any on a living mammal by the effective administration of a drug to a patient wherein the effects are clinically detectable and determinable in the mammal's triglyceride cycling system utilizing an inhibitor of $iPLA_2$epsilon. In an aspect the invention comprises administering a drug to a living mammal to effect or modulate the triglyceride cycling system using an $iPLA_2$epsilon inhibitor. In an aspect the invention comprises delivering a compound to a mammal wherein the compound is delivered to the mammal to effect the futile cycle.

In an aspect, a method of TAG analysis and lipid analysis useful in this invention is carried out by using a method disclosed in U.S. patent application Ser. No. 10/606,601 filed Jun. 26, 2003, "Spectrometric Quantitation of Triglyceride Molecular Species", Publication No. 2004-0063118, published Apr. 1, 2004 which is incorporated herein by reference in its entirety. A level of expression greater or less than expression in an absence of the substance selected to be measured indicates and is determinant of activity in modulating $iPLA_{2\epsilon}$ expression.

In a first embodiment, in regard to the method of analysis disclosed in U.S. Ser. No. 10/606,601 filed Jun. 26, 2003, the content of which are incorporated herein by reference, a method for the determination of TG individual (i.e. separate) molecular species in a composition of matter such as the above in a biological sample comprises subjecting the biological sample to lipid extraction to obtain a lipid extract and subjecting the lipid extract to electrospray ionization tandem mass spectrometry (ESI/MS/MS) providing TG molecular species composition as a useful output determination.

In an aspect, our inventive concept comprises analyzing a biological sample using electrospray ionization tandem mass spectrometry (ESI/MS/MS) and performing a two dimensional analysis with cross peak contour analysis on the output of the ESI/MS/MS to provide a fingerprint triglyceride individual (i.e. separate) molecular species.

Briefly, the inventive methods present a novel two-dimensional approach/method which quantitates individual molecular species of triglycerides by two dimensional electrospray ionization mass spectroscopy with neutral loss scanning. This method is also useful for polar lipid analysis by ESI/MS using conditions as outlined in U.S. Ser. No. 10/606, 601 (see above filed Jun. 26, 2003, the contents of which are incorporated herein by reference) and is protected by a provisional patent and be reference herein. This method provides a facile way to fingerprint each patient's (or biologic samples) triglyceride composition of matter (individual molecular species content) and lipid composition of matter directly from chloroform extracts of biologic samples. Through selective ionization and subsequent deconvolution of 2D intercept density contours of the pseudomolecular parent ions and their neutral loss products, the individual molecular species of triglycerides and phospholipids can be determined directly from chloroform extracts of biological material. This 2D (two dimensional) approach comprises a novel enhanced successful functional therapy model for the automated determination and global fingerprinting of each patient's serum or cellular triglyceride and phospholipid profile content thus providing the facile determination of detailed aspects of lipid metabolism underlying disease states and their response to diet, exercise or drug therapy.

In an aspect of this inventive method, tandem mass spectroscopic separation of specific lipid class-reagent ion pairs is used in conjunction with contour density deconvolution of cross peaks resulting from neutral losses of aliphatic chains to determine the individual triglyceride molecular species from a biological sample (blood, liver, muscle, feces, urine, tissue biopsy, or rat myocardium).

In an aspect, a biological sample is processed in tandem mass spectrometer a first mass spectrometer set up in a tandem arrangement with another mass spectrometer. In that regard the biological sample can be considered as sorted and weighed in the first mass spectrometer, then broken into parts in an inter-mass spectrometer collision cell, and a part or parts of the biological sample are thereafter sorted and weighed in the second mass spectrometer thereby providing a mass spectrometric output readily and directly useable from the tandem mass spectrometer.

In an aspect, a pre-analysis separation comprises a separation of lipoproteins prior to lipid extraction. In an aspect, the pre-analysis separation comprises at least one operation or process which is useful to provide an enhanced biological sample to the electrospray ionization tandem mass spectrometry (ESI/MS/MS). In an aspect, a pre-analysis separation is performed on a biological sample and two compositions are prepared accordingly from the biological sample. In an aspect one composition comprises high density lipoproteins and another composition comprises low density lipoproteins and variants thereof comprised of intermediate densities which can, if necessary, be resolved by chromatographic or other density techniques.

Generally, a biological sample taken is representative of the subject from which or of which the sample is taken so that an analysis of the sample is representative of the subject. In an aspect a representative number of samples are taken and analyzed of a subject such that a recognized and accepted statistical analysis indicates that the analytic results are statistically valid. Typically the composition is aqueous based and contains proteinaceous matter along with triglycerides. For example, a human blood sample is sometimes used. Through use of this inventive method, a plasma sample can be analyzed and appropriate information from the plasma can be extracted in a few minutes. Alternatively, information can be taken from the cells in the blood as well.

In an aspect, serum is utilized as a biological sample. After whole blood is removed from a human body and the blood clots outside the body, blood cells and some of the proteins become solid leaving a residual liquid which is serum.

In an aspect a control sample is employed in the analysis.

In an aspect, the biological sample or a representative aliquot or portion thereof is subjected to lipid extraction to obtain a lipid extract suitable for ESI/MS/MS. In an aspect lipids are extracted from the sample which in an aspect contains a tissue matrix. Non-lipid contaminants should be removed from the lipid extract.

In one aspect lipid extraction is carried by the known lipid extraction process of Folch as well as by the known lipid extraction process of Bligh and Dyer. These useful lipid extraction process are described in Christie, W. W. Preparation of lipid extracts from tissues. In: Advances in Lipid Methodology—Two, pp. 195-213 (1993) (edited by W. W. Christie, Oily Press, Dundee) EXTRACTION OF LIPIDS FROM SAMPLES William W. Christie The Scottish Crop Research Institute, Invergowrie, Dundee DD2 5DA, Scotland all of which are incorporated herein in their entirety by reference. The useful Folch extraction process is incorporated herein in its entirety by reference (13).

Generally, lipid extraction is carried out very soon in time on the tissue matrix or immediately after removel (harvest) of tissues (tissue matrix) from humanely sacrificed organisms which have been living (carried out using and following acceptable animal welfare protocols). Alternatively, tissues are stored in such a way that they are conservatively preserved for future use. In an aspect, a lipid extract is provided and used to produce ionized atoms and molecules in the inventive analytical method as feed to the ESI mass spectrometer in our novel analysis method.

In an aspect a chloroform lipid extract is employed as a lipid extract composition fed to the ESI mass spectrometer. The effluent from the ESI is fed to the tandem mass spectrometer (i.e. from the exit of the ESI).

In an aspect, a Freezer Mill 6800 from Fisher Bioblock Scientific is used to finely pulverize soft or hard harvested tissues of a representative biological sample in one or two minutes in liquid nitrogen to render the tissue sufficiently pliable and porous for lipid extraction. Alternatively, the pulverization of the harvested tissue is carried out by subjecting the harvested tissue to hand directed mashing and pulverization using a hand directed stainless-steel mortar and pestle. In a further aspect, an enzymatic digestion is carried out on the harvested tissue which is harvested from a preserved cadaver.

In an aspect, lipids are contained in the lipid extract following the lipid extraction. Generally the extraction is a suitable liquid/liquid or liquid/solid extraction whereby the TGs are contained in the extract. In an aspect the extractant has sufficient solvating capability power and solvating capacity so as to solvate a substantial portion of the TG therein or substantially all of the TG present in the biological sample and is contained in the lipid extract.

In an aspect, chloroform is employed as an extractant to produce a useful lipid extract. Other useful extractants include but are not limited to those extractants which have a solvating power, capability and efficiency substantially that of chloroform with regard to the TG molecular species.

The inventive process creates charged forms of very high molecular weight TG molecules obtained via lipid extraction of a biological sample as a part of the process of detecting and analyzing biological samples containing TG.

In an aspect, in order to detect for and analyze ionized atoms and molecules such as TG molecular species in a biological sample, the lipid extract of that biological sample is used to produce ionized atoms and molecules by an ionization method such as electrospray ionization (ESI). As used herein, the term ESI includes both conventional and pneumatically-assisted electrospray mass spectrometry.

In use, the inventive procedure operates by producing droplets of a sample composition by pneumatic nebulization which compresses and forces a biological sample composition containing TG such as an analyte containing TG into a proximal end of a mechanical means housing or holding a fine sized orifice such as a needle or capillary exiting at the distal end of the orifice at which there is applied a sufficient potential. Generally the orifice is a very small bore full length orifice having an internal average diameter or bore in the range from about 0.2 to about 0.5 mm.

In an aspect, formation of a suitable spray is a critical operating parameter in ESI. Suitable solvent removable filters may be used to remove undesired solvents in the biological sample composition prior to being fed to the ESI. Generally high concentrations of electrolytes are avoided in samples fed to ESI.

The composition of materials of the means housing or holding the orifice and the orifice are compatible with the compositions of the biological sample to be processed through the orifice. Metallic and composition plastic compositions may be employed. In an aspect the orifice is a capillary or has a conical or capillary shape. In another aspect the orifice is cone shaped with the exterior converging from the proximate end to the distal end.

In an aspect, the biologic sample is forced through the orifice by application of air pressure to the sample at the proximate end of the orifice or the sample is forced through the orifice or capillary by the application of vacuum at the distal end of the orifice. The net result is that ions are suitably formed at atmospheric pressure and progress through the cone shaped orifice. In an aspect the orifice is a first vacuum stage and the ions undergo free jet expansion. A collector at the distal end of the orifice collects the ions and guides the ions to a tandem mass spectrometer (MS/MS).

REFERENCES

1. Baulande, S., Lasnier, F., Lucas, M., and Pairault, J. (2001) *J. Bid. Chem.* 276, 33336-33444

2. Polson, D. and Thompson, M. P. (2003) *Biochem. Biophys. Res. Comm.* 301, 261-266

3. Frost, S. C., and Lane, M. D. (1985) *J Biol Chem* 260, 2646-2652

4. Izem, L., and Morton, R. E. (2001) *J Biol Chem* 276, 26534-26541

5. Laemmli, U. K. (1970) *Nature* 227, 680-685

6. Polson, D. and Thompson, M. P. (2003) *Horm. Metab. Res.* 35, 508-510

7. Poison, D. A., and Thompson, M. P. (2004) *J Nutr Biochem* 15, 242-246

8. Haemmerle, G., Zimmermann, R., Hayn, M., Theussl, C., Waeg, G., Wagner, E., Sattler, W., Magin, T. M., Wagner, E. F., and Zechner, R. (2002) *J Biol Chem* 277, 4806-4815

9. Osuga, J., Ishibashi, S., Oka, T., Yagyu, H., Tozawa, R., Fujimoto; A., Shionoiri, F., Yahagi, N., Kraemer, F. B., Tsutsumi, O., and Yamada, N. (2000) *Proc Natl Acad Sci USA* 97, 787-792

10. Wang, S. P., Laurin, N., Himms-Hagen, J., Rudnicki, M. A., Levy, E., Robert, M. F., Pan, L., Oligny, L., and Mitchell, G. A. (2001) *Obes Res* 9, 119-128

11. Okazaki, H., Osuga, J., Tamura, Y., Yahagi, N., Tomita, S., Shionoiri, F., Iizuka, Y., Ohashi, K., Harada, K., Kimura, S., Gotoda, T., Shimano, H., Yamada, N., and Ishibashi, S. (2002) *Diabetes* 51, 3368-3375

12. Reshef, L., Olswang, Y., Cassuto, H., Blum, B., Croniger, C. M., Kalhan, S. C., Tilghman, S. M., and Hanson, R. W. (2003) *J Biol. Chem.* 278, 30413-30416

13. Folch, J., Lees, M., and Stanley, G. H. S. (1957) *J Biol Chem* 226, 497-509

Lehner, R., and Kuksis, A. (1993) *J Biol Chem* 268, 8781-8786

Jenkins, C. M., Mancuso, D. J., Yan, W., Sims, H. F., Gibson, B., and Gross, R. W. (2004) *J Biol Chem* 279, 48968-75

While the discovery has been described in terms of various specific embodiments, those skilled in the art will recognize that the discovery can be practiced with modification within the spirit and scope of the discovery.

What is claimed:

1. An isolated nucleic acid molecule comprising a calcium-independent phospholipase $A_2\epsilon$ polynucleotide having nucleic acid sequences SEQ ID NO: 3 and SEQ ID NO: 4, wherein SEQ ID NO: 3 encodes a calcium-independent phospholipase $A_2\epsilon$ polypeptide having SEQ ID NO: 1, and SEQ ID NO: 4 encodes a calcium-independent phospholipase $A_2\epsilon$ polypeptide having SEQ ID NO: 2.

2. An isolated gene comprising a polynucleotide having a sequence shown in SEQ ID NO: 3 and a sequence shown in SEQ ID NO: 4.

3. A genetically engineered expression vector comprising a gene or part of a sequence of the gene comprising a polynucleotide having a sequence shown in SEQ ID NO: 3 and a polynucleotide having a sequence shown in SEQ ID NO: 4.

4. A genetically engineered expression vector in accordance with claim 3, wherein the gene encodes a protein comprising a polypeptide having a sequence shown in SEQ ID NO: 2.

5. A genetically engineered expression vector in accordance with claim 4 wherein the gene is operatively linked to a promoter element.

6. A genetically engineered expression vector in accordance with claim 3, wherein the gene encodes a protein comprising a polypeptide having a sequence shown in SEQ ID NO: 1.

7. A genetically engineered expression vector in accordance with claim 6, wherein the gene is operatively linked to a promoter element.

8. An isolated nucleic acid molecule comprising a calcium-independent phospholipase $A_{2\epsilon}$ polynucleotide having SEQ ID NO: 4, wherein SEQ ID NO: 4 encodes a calcium-independent phospholipase A2ϵ polypeptide having SEQ ID NO: 2.

9. A genetically engineered expression vector comprising a gene or part of a sequence of the gene comprising a polynucleotide having the sequence shown in SEQ ID NO: 4.

10. A genetically engineered expression vector in accordance with claim 9, wherein the gene encodes a polypeptide having the sequence shown in SEQ ID NO: 2.

11. A genetically engineered expression vector in accordance with claim 10, wherein the gene is operatively linked to a promoter element.

12. An isolated gene comprising a polynucleotide having the sequence shown in SEQ ID NO: 4.

* * * * *

SEQUENCE LISTING

```
<160> NUMBER OF SEQ ID NOS: 20

<210> SEQ ID NO 1
<211> LENGTH: 481
<212> TYPE: PRT
<213> ORGANISM: Homo sapiens

<400> SEQUENCE: 1

Met Tyr Asp Ala Glu Arg Gly Trp Ser Leu Ser Phe Ala Gly Cys Gly
1               5                   10                  15

Phe Leu Gly Phe Tyr His Val Gly Ala Thr Arg Cys Leu Ser Glu His
            20                  25                  30

Ala Pro His Leu Leu Arg Asp Ala Arg Met Leu Phe Gly Ala Ser Ala
        35                  40                  45

Gly Ala Leu His Cys Val Gly Val Leu Ser Gly Ile Pro Leu Glu Gln
    50                  55                  60

Thr Leu Gln Val Leu Ser Asp Leu Val Arg Lys Ala Arg Ser Arg Asn
65                  70                  75                  80

Ile Gly Ile Phe His Pro Ser Phe Asn Leu Ser Lys Phe Leu Arg Gln
                85                  90                  95
```

-continued

```
Gly Leu Cys Lys Cys Leu Pro Ala Asn Val His Gln Leu Ile Ser Gly
            100                 105                 110

Lys Ile Gly Ile Ser Leu Thr Arg Val Ser Asp Gly Glu Asn Val Leu
        115                 120                 125

Val Ser Asp Phe Arg Ser Lys Asp Glu Val Val Asp Ala Leu Val Cys
    130                 135                 140

Ser Cys Phe Ile Pro Phe Tyr Ser Gly Leu Ile Pro Pro Ser Phe Arg
145                 150                 155                 160

Gly Val Arg Tyr Val Asp Gly Gly Val Ser Asp Asn Val Pro Phe Ile
                165                 170                 175

Asp Ala Lys Thr Thr Ile Thr Val Ser Pro Phe Tyr Gly Glu Tyr Asp
            180                 185                 190

Ile Cys Pro Lys Val Lys Ser Thr Asn Phe Leu His Val Asp Ile Thr
        195                 200                 205

Lys Leu Ser Leu Arg Leu Cys Thr Gly Asn Leu Tyr Leu Leu Ser Arg
    210                 215                 220

Ala Phe Val Pro Pro Asp Leu Lys Val Leu Gly Glu Ile Cys Leu Arg
225                 230                 235                 240

Gly Tyr Leu Asp Ala Phe Arg Phe Leu Glu Glu Lys Gly Ile Cys Asn
                245                 250                 255

Arg Pro Gln Pro Gly Leu Lys Ser Ser Ser Glu Gly Met Asp Pro Glu
            260                 265                 270

Val Ala Met Pro Ser Trp Ala Asn Met Ser Leu Asp Ser Ser Pro Glu
        275                 280                 285

Ser Ala Ala Leu Ala Val Arg Leu Glu Gly Asp Glu Leu Leu Asp His
    290                 295                 300

Leu Arg Leu Ser Ile Leu Pro Trp Asp Glu Ser Ile Leu Asp Thr Leu
305                 310                 315                 320

Ser Pro Arg Leu Ala Thr Ala Leu Ser Glu Glu Met Lys Asp Lys Gly
                325                 330                 335

Gly Tyr Met Ser Lys Ile Cys Asn Leu Leu Pro Ile Arg Ile Met Ser
            340                 345                 350

Tyr Val Met Leu Pro Cys Thr Leu Pro Val Glu Ser Ala Ile Ala Ile
        355                 360                 365

Val Gln Arg Leu Val Thr Trp Leu Pro Asp Met Pro Asp Asp Val Leu
    370                 375                 380

Trp Leu Gln Trp Val Thr Ser Gln Val Phe Thr Arg Val Leu Met Cys
385                 390                 395                 400

Leu Leu Pro Ala Ser Arg Ser Gln Met Pro Val Ser Ser Gln Gln Ala
                405                 410                 415

Ser Pro Cys Thr Pro Glu Gln Asp Trp Pro Cys Trp Thr Pro Cys Ser
            420                 425                 430

Pro Glu Gly Cys Pro Ala Glu Thr Lys Ala Glu Ala Thr Pro Arg Ser
        435                 440                 445

Ile Leu Arg Ser Ser Leu Asn Phe Phe Leu Gly Asn Lys Val Pro Ala
    450                 455                 460

Gly Ala Glu Gly Leu Ser Thr Phe Pro Ser Phe Ser Leu Glu Lys Ser
465                 470                 475                 480

Leu
```

<210> SEQ ID NO 2
<211> LENGTH: 481
<212> TYPE: PRT
<213> ORGANISM: Homo sapiens

<400> SEQUENCE: 2

```
Met Tyr Asp Ala Glu Arg Gly Trp Ser Leu Ser Phe Ala Gly Cys Gly
1               5                   10                  15

Phe Leu Gly Phe Tyr His Val Gly Ala Thr Arg Cys Leu Ser Glu His
            20                  25                  30

Ala Pro His Leu Leu Arg Asp Ala Arg Met Leu Phe Gly Ala Ser Ala
        35                  40                  45

Gly Ala Leu His Cys Val Gly Val Leu Ser Gly Ile Pro Leu Glu Gln
    50                  55                  60

Thr Leu Gln Val Leu Ser Asp Leu Val Arg Lys Ala Arg Ser Arg Asn
65                  70                  75                  80

Ile Gly Ile Phe His Pro Ser Phe Asn Leu Ser Lys Phe Leu Arg Gln
                85                  90                  95

Gly Leu Cys Lys Cys Leu Pro Ala Asn Val His Gln Leu Ile Ser Gly
            100                 105                 110

Lys Ile Gly Ile Ser Leu Thr Arg Val Ser Asp Gly Glu Asn Val Leu
        115                 120                 125

Val Ser Asp Phe Arg Ser Lys Asp Glu Val Val Asp Ala Leu Val Cys
    130                 135                 140

Ser Cys Phe Ile Pro Phe Tyr Ser Gly Leu Ile Pro Pro Ser Phe Arg
145                 150                 155                 160

Gly Val Arg Tyr Val Asp Gly Gly Val Ser Asp Asn Val Pro Phe Ile
                165                 170                 175

Asp Ala Lys Thr Thr Ile Thr Val Ser Pro Phe Tyr Gly Glu Tyr Asp
            180                 185                 190

Ile Cys Pro Lys Val Lys Ser Thr Asn Phe Leu His Val Asp Ile Thr
        195                 200                 205

Lys Leu Ser Leu Arg Leu Cys Thr Gly Asn Leu Tyr Leu Leu Ser Arg
    210                 215                 220

Ala Phe Val Pro Pro Asp Leu Lys Val Leu Gly Glu Ile Cys Leu Arg
225                 230                 235                 240

Gly Tyr Leu Asp Ala Phe Arg Phe Leu Glu Glu Lys Gly Ile Cys Asn
                245                 250                 255

Arg Pro Gln Pro Gly Leu Lys Ser Ser Ser Glu Gly Met Asp Pro Glu
            260                 265                 270

Val Ala Met Pro Ser Trp Ala Asn Met Ser Leu Asp Ser Ser Pro Glu
        275                 280                 285

Ser Ala Ala Leu Ala Val Arg Leu Glu Gly Asp Glu Leu Leu Asp His
    290                 295                 300

Leu Arg Leu Ser Ile Leu Pro Trp Asp Glu Ser Ile Leu Asp Thr Leu
305                 310                 315                 320

Ser Pro Arg Leu Ala Thr Ala Leu Ser Glu Glu Met Lys Asp Lys Gly
                325                 330                 335

Gly Tyr Met Ser Lys Ile Cys Asn Leu Leu Pro Ile Arg Ile Met Ser
            340                 345                 350

Tyr Val Met Leu Pro Cys Thr Leu Pro Val Glu Ser Ala Ile Ala Ile
        355                 360                 365

Val Gln Arg Leu Val Thr Trp Leu Pro Asp Met Pro Asp Asp Val Leu
    370                 375                 380

Trp Leu Gln Trp Val Thr Ser Gln Val Phe Thr Arg Val Leu Met Cys
385                 390                 395                 400

Leu Leu Pro Ala Ser Arg Ser Gln Met Pro Val Ser Ser Gln Gln Ala
                405                 410                 415
```

-continued

```
Ser Pro Cys Thr Pro Glu Gln Asp Trp Pro Cys Trp Thr Pro Cys Ser
            420                 425                 430

Pro Lys Gly Cys Pro Ala Glu Thr Lys Ala Glu Ala Thr Pro Arg Ser
        435                 440                 445

Ile Leu Arg Ser Ser Leu Asn Phe Phe Leu Gly Asn Lys Val Pro Ala
    450                 455                 460

Gly Ala Glu Gly Leu Ser Thr Phe Pro Ser Phe Ser Leu Glu Lys Ser
465                 470                 475                 480

Leu


<210> SEQ ID NO 3
<211> LENGTH: 1446
<212> TYPE: DNA
<213> ORGANISM: Homo sapiens
<220> FEATURE:
<221> NAME/KEY: CDS
<222> LOCATION: (1)..(1443)

<400> SEQUENCE: 3

atg tac gac gca gag cgc ggc tgg agc ttg tcc ttc gcg ggc tgc ggc       48
Met Tyr Asp Ala Glu Arg Gly Trp Ser Leu Ser Phe Ala Gly Cys Gly
  1               5                  10                  15

ttc ctg ggc ttc tac cac gtc ggg gcg acc cgc tgc ctg agc gag cac       96
Phe Leu Gly Phe Tyr His Val Gly Ala Thr Arg Cys Leu Ser Glu His
             20                  25                  30

gcc ccg cac ctc ctc cgc gac gcg cgc atg ttg ttc ggc gct tcg gcc      144
Ala Pro His Leu Leu Arg Asp Ala Arg Met Leu Phe Gly Ala Ser Ala
         35                  40                  45

ggg gcg ttg cac tgc gtc ggc gtc ctc tcc ggt atc ccg ctg gag cag      192
Gly Ala Leu His Cys Val Gly Val Leu Ser Gly Ile Pro Leu Glu Gln
     50                  55                  60

act ctg cag gtc ctc tca gat ctt gtg cgg aag gcc agg agt cgg aac      240
Thr Leu Gln Val Leu Ser Asp Leu Val Arg Lys Ala Arg Ser Arg Asn
 65                  70                  75                  80

att ggc atc ttc cat cca tcc ttc aac tta agc aag ttc ctc cga cag      288
Ile Gly Ile Phe His Pro Ser Phe Asn Leu Ser Lys Phe Leu Arg Gln
                 85                  90                  95

ggt ctc tgc aaa tgc ctc ccg gcc aat gtc cac cag ctc atc tcc ggc      336
Gly Leu Cys Lys Cys Leu Pro Ala Asn Val His Gln Leu Ile Ser Gly
            100                 105                 110

aaa ata ggc atc tct ctt acc aga gtg tct gat ggg gaa aac gtt ctg      384
Lys Ile Gly Ile Ser Leu Thr Arg Val Ser Asp Gly Glu Asn Val Leu
        115                 120                 125

gtg tct gac ttt cgg tcc aaa gac gaa gtc gtg gat gcc ttg gta tgt      432
Val Ser Asp Phe Arg Ser Lys Asp Glu Val Val Asp Ala Leu Val Cys
    130                 135                 140

tcc tgc ttc atc ccc ttc tac agt ggc ctt atc cct cct tcc ttc aga      480
Ser Cys Phe Ile Pro Phe Tyr Ser Gly Leu Ile Pro Pro Ser Phe Arg
145                 150                 155                 160

ggc gtg cga tat gtg gat gga gga gtg agt gac aac gta ccc ttc att      528
Gly Val Arg Tyr Val Asp Gly Gly Val Ser Asp Asn Val Pro Phe Ile
                165                 170                 175

gat gcc aaa aca acc atc acc gtg tcc ccc ttc tat ggg gag tac gac      576
Asp Ala Lys Thr Thr Ile Thr Val Ser Pro Phe Tyr Gly Glu Tyr Asp
            180                 185                 190

atc tgc cct aaa gtc aag tcc acg aac ttt ctt cat gtg gac atc acc      624
Ile Cys Pro Lys Val Lys Ser Thr Asn Phe Leu His Val Asp Ile Thr
        195                 200                 205
```

-continued

```
aag ctc agt cta cgc ctc tgc aca ggg aac ctc tac ctt ctc tcg aga      672
Lys Leu Ser Leu Arg Leu Cys Thr Gly Asn Leu Tyr Leu Leu Ser Arg
    210                 215                 220

gct ttt gtc ccc ccg gat ctc aag gtg ctg gga gag ata tgc ctt cga      720
Ala Phe Val Pro Pro Asp Leu Lys Val Leu Gly Glu Ile Cys Leu Arg
225                 230                 235                 240

gga tat ttg gat gca ttc agg ttc ttg gaa gag aag ggc atc tgc aac      768
Gly Tyr Leu Asp Ala Phe Arg Phe Leu Glu Glu Lys Gly Ile Cys Asn
                245                 250                 255

agg ccc cag cca ggc ctg aag tca tcc tca gaa ggg atg gat cct gag      816
Arg Pro Gln Pro Gly Leu Lys Ser Ser Ser Glu Gly Met Asp Pro Glu
            260                 265                 270

gtc gcc atg ccc agc tgg gca aac atg agt ctg gat tct tcc ccg gag      864
Val Ala Met Pro Ser Trp Ala Asn Met Ser Leu Asp Ser Ser Pro Glu
        275                 280                 285

tcg gct gcc ttg gct gtg agg ctg gag gga gat gag ctg cta gac cac      912
Ser Ala Ala Leu Ala Val Arg Leu Glu Gly Asp Glu Leu Leu Asp His
    290                 295                 300

ctg cgt ctc agc atc ctg ccc tgg gat gag agc atc ctg gac acc ctc      960
Leu Arg Leu Ser Ile Leu Pro Trp Asp Glu Ser Ile Leu Asp Thr Leu
305                 310                 315                 320

tcg ccc agg ctc gct aca gca ctg agt gaa gaa atg aaa gac aaa ggt     1008
Ser Pro Arg Leu Ala Thr Ala Leu Ser Glu Glu Met Lys Asp Lys Gly
                325                 330                 335

gga tac atg agc aag att tgc aac ttg cta ccc att agg ata atg tct     1056
Gly Tyr Met Ser Lys Ile Cys Asn Leu Leu Pro Ile Arg Ile Met Ser
            340                 345                 350

tat gta atg ctg ccc tgt acc ctg cct gtg gaa tct gcc att gcg att     1104
Tyr Val Met Leu Pro Cys Thr Leu Pro Val Glu Ser Ala Ile Ala Ile
        355                 360                 365

gtc cag aga ctg gtg aca tgg ctt cca gat atg ccc gac gat gtc ctg     1152
Val Gln Arg Leu Val Thr Trp Leu Pro Asp Met Pro Asp Asp Val Leu
    370                 375                 380

tgg ttg cag tgg gtg acc tca cag gtg ttc act cga gtg ctg atg tgt     1200
Trp Leu Gln Trp Val Thr Ser Gln Val Phe Thr Arg Val Leu Met Cys
385                 390                 395                 400

ctg ctc ccc gcc tcc agg tcc caa atg cca gtg agc agc caa cag gcc     1248
Leu Leu Pro Ala Ser Arg Ser Gln Met Pro Val Ser Ser Gln Gln Ala
                405                 410                 415

tcc cca tgc aca cct gag cag gac tgg ccc tgc tgg act ccc tgc tcc     1296
Ser Pro Cys Thr Pro Glu Gln Asp Trp Pro Cys Trp Thr Pro Cys Ser
            420                 425                 430

ccc gag ggc tgt cca gca gag acc aaa gca gag gcc acc ccg cgg tcc     1344
Pro Glu Gly Cys Pro Ala Glu Thr Lys Ala Glu Ala Thr Pro Arg Ser
        435                 440                 445

atc ctc agg tcc agc ctg aac ttc ttc ttg ggc aat aaa gta cct gct     1392
Ile Leu Arg Ser Ser Leu Asn Phe Phe Leu Gly Asn Lys Val Pro Ala
    450                 455                 460

ggt gct gag ggg ctc tcc acc ttt ccc agt ttt tca cta gag aag agt     1440
Gly Ala Glu Gly Leu Ser Thr Phe Pro Ser Phe Ser Leu Glu Lys Ser
465                 470                 475                 480

ctg tga                                                             1446
Leu


<210> SEQ ID NO 4
<211> LENGTH: 1446
<212> TYPE: DNA
<213> ORGANISM: Homo sapiens
<220> FEATURE:
<221> NAME/KEY: CDS
<222> LOCATION: (1)..(1443)
```

```
<400> SEQUENCE: 4

atg tac gac gca gag cgc ggc tgg agc ttg tcc ttc gcg ggc tgc ggc        48
Met Tyr Asp Ala Glu Arg Gly Trp Ser Leu Ser Phe Ala Gly Cys Gly
  1               5                  10                  15

ttc ctg ggc ttc tac cac gtc ggg gcg acc cgc tgc ctg agc gag cac        96
Phe Leu Gly Phe Tyr His Val Gly Ala Thr Arg Cys Leu Ser Glu His
             20                  25                  30

gcc ccg cac ctc ctc cgc gac gcg cgc atg ttg ttc ggc gct tcg gcc       144
Ala Pro His Leu Leu Arg Asp Ala Arg Met Leu Phe Gly Ala Ser Ala
         35                  40                  45

ggg gcg ttg cac tgc gtc ggc gtc ctc tcc ggt atc ccg ctg gag cag       192
Gly Ala Leu His Cys Val Gly Val Leu Ser Gly Ile Pro Leu Glu Gln
     50                  55                  60

act ctg cag gtc ctc tca gat ctt gtg cgg aag gcc agg agt cgg aac       240
Thr Leu Gln Val Leu Ser Asp Leu Val Arg Lys Ala Arg Ser Arg Asn
 65                  70                  75                  80

att ggc atc ttc cat cca tcc ttc aac tta agc aag ttc ctc cga cag       288
Ile Gly Ile Phe His Pro Ser Phe Asn Leu Ser Lys Phe Leu Arg Gln
                 85                  90                  95

ggt ctc tgc aaa tgc ctc ccg gcc aat gtc cac cag ctc atc tcc ggc       336
Gly Leu Cys Lys Cys Leu Pro Ala Asn Val His Gln Leu Ile Ser Gly
            100                 105                 110

aaa ata ggc atc tct ctt acc aga gtg tct gat ggg gaa aac gtt ctg       384
Lys Ile Gly Ile Ser Leu Thr Arg Val Ser Asp Gly Glu Asn Val Leu
        115                 120                 125

gtg tct gac ttt cgg tcc aaa gac gaa gtc gtg gat gcc ttg gta tgt       432
Val Ser Asp Phe Arg Ser Lys Asp Glu Val Val Asp Ala Leu Val Cys
    130                 135                 140

tcc tgc ttc atc ccc ttc tac agt ggc ctt atc cct cct tcc ttc aga       480
Ser Cys Phe Ile Pro Phe Tyr Ser Gly Leu Ile Pro Pro Ser Phe Arg
145                 150                 155                 160

ggc gtg cga tat gtg gat gga gga gtg agt gac aac gta ccc ttc att       528
Gly Val Arg Tyr Val Asp Gly Gly Val Ser Asp Asn Val Pro Phe Ile
                165                 170                 175

gat gcc aaa aca acc atc acc gtg tcc ccc ttc tat ggg gag tac gac       576
Asp Ala Lys Thr Thr Ile Thr Val Ser Pro Phe Tyr Gly Glu Tyr Asp
            180                 185                 190

atc tgc cct aaa gtc aag tcc acg aac ttt ctt cat gtg gac atc acc       624
Ile Cys Pro Lys Val Lys Ser Thr Asn Phe Leu His Val Asp Ile Thr
        195                 200                 205

aag ctc agt cta cgc ctc tgc aca ggg aac ctc tac ctt ctc tcg aga       672
Lys Leu Ser Leu Arg Leu Cys Thr Gly Asn Leu Tyr Leu Leu Ser Arg
    210                 215                 220

gct ttt gtc ccc ccg gat ctc aag gtg ctg gga gag ata tgc ctt cga       720
Ala Phe Val Pro Pro Asp Leu Lys Val Leu Gly Glu Ile Cys Leu Arg
225                 230                 235                 240

gga tat ttg gat gca ttc agg ttc ttg gaa gag aag ggc atc tgc aac       768
Gly Tyr Leu Asp Ala Phe Arg Phe Leu Glu Glu Lys Gly Ile Cys Asn
                245                 250                 255

agg ccc cag cca ggc ctg aag tca tcc tca gaa ggg atg gat cct gag       816
Arg Pro Gln Pro Gly Leu Lys Ser Ser Ser Glu Gly Met Asp Pro Glu
            260                 265                 270

gtc gcc atg ccc agc tgg gca aac atg agt ctg gat tct tcc ccg gag       864
Val Ala Met Pro Ser Trp Ala Asn Met Ser Leu Asp Ser Ser Pro Glu
        275                 280                 285

tcg gct gcc ttg gct gtg agg ctg gag gga gat gag ctg cta gac cac       912
Ser Ala Ala Leu Ala Val Arg Leu Glu Gly Asp Glu Leu Leu Asp His
    290                 295                 300
```

```
ctg cgt ctc agc atc ctg ccc tgg gat gag agc atc ctg gac acc ctc      960
Leu Arg Leu Ser Ile Leu Pro Trp Asp Glu Ser Ile Leu Asp Thr Leu
305                 310                 315                 320

tcg ccc agg ctc gct aca gca ctg agt gaa gaa atg aaa gac aaa ggt     1008
Ser Pro Arg Leu Ala Thr Ala Leu Ser Glu Glu Met Lys Asp Lys Gly
                325                 330                 335

gga tac atg agc aag att tgc aac ttg cta ccc att agg ata atg tct     1056
Gly Tyr Met Ser Lys Ile Cys Asn Leu Leu Pro Ile Arg Ile Met Ser
            340                 345                 350

tat gta atg ctg ccc tgt acc ctg cct gtg gaa tct gcc att gcg att     1104
Tyr Val Met Leu Pro Cys Thr Leu Pro Val Glu Ser Ala Ile Ala Ile
        355                 360                 365

gtc cag aga ctg gtg aca tgg ctt cca gat atg ccc gac gat gtc ctg     1152
Val Gln Arg Leu Val Thr Trp Leu Pro Asp Met Pro Asp Asp Val Leu
    370                 375                 380

tgg ttg cag tgg gtg acc tca cag gtg ttc act cga gtg ctg atg tgt     1200
Trp Leu Gln Trp Val Thr Ser Gln Val Phe Thr Arg Val Leu Met Cys
385                 390                 395                 400

ctg ctc ccc gcc tcc agg tcc caa atg cca gtg agc agc caa cag gcc     1248
Leu Leu Pro Ala Ser Arg Ser Gln Met Pro Val Ser Ser Gln Gln Ala
                405                 410                 415

tcc cca tgc aca cct gag cag gac tgg ccc tgc tgg act ccc tgc tcc     1296
Ser Pro Cys Thr Pro Glu Gln Asp Trp Pro Cys Trp Thr Pro Cys Ser
            420                 425                 430

ccc aag ggc tgt cca gca gag acc aaa gca gag gcc acc ccg cgg tcc     1344
Pro Lys Gly Cys Pro Ala Glu Thr Lys Ala Glu Ala Thr Pro Arg Ser
        435                 440                 445

atc ctc agg tcc agc ctg aac ttc ttc ttg ggc aat aaa gta cct gct     1392
Ile Leu Arg Ser Ser Leu Asn Phe Phe Leu Gly Asn Lys Val Pro Ala
    450                 455                 460

ggt gct gag ggg ctc tcc acc ttt ccc agt ttt tca cta gag aag agt     1440
Gly Ala Glu Gly Leu Ser Thr Phe Pro Ser Phe Ser Leu Glu Lys Ser
465                 470                 475                 480

ctg tga                                                             1446
Leu


<210> SEQ ID NO 5
<211> LENGTH: 44
<212> TYPE: PRT
<213> ORGANISM: Solanum tuberosum

<400> SEQUENCE: 5

Gly Gly Gly Ile Lys Gly Ile Ile Pro Ala Ile Ile Leu Glu Phe Leu
  1               5                  10                  15

Glu Gly Gln Leu Gln Glu Val Asp Asn Asn Lys Asp Ala Arg Leu Ala
             20                  25                  30

Asp Tyr Phe Asp Val Ile Gly Gly Thr Ser Thr Gly
         35                  40


<210> SEQ ID NO 6
<211> LENGTH: 37
<212> TYPE: PRT
<213> ORGANISM: Mus sp.

<400> SEQUENCE: 6

Gly Gly Gly Val Lys Gly Leu Val Ile Ile Gln Leu Leu Ile Ala Ile
  1               5                  10                  15
```

-continued

```
Glu Lys Ala Ser Gly Val Ala Thr Lys Asp Leu Phe Asp Trp Val Ala
            20                  25                  30

Gly Thr Ser Thr Gly
        35


<210> SEQ ID NO 7
<211> LENGTH: 37
<212> TYPE: PRT
<213> ORGANISM: Homo sapiens

<400> SEQUENCE: 7

Gly Gly Gly Thr Arg Gly Val Val Ala Leu Gln Thr Leu Arg Lys Leu
  1               5                  10                  15

Val Glu Leu Thr Gln Lys Pro Val His Gln Leu Phe Asp Tyr Ile Cys
            20                  25                  30

Gly Val Ser Thr Gly
        35


<210> SEQ ID NO 8
<211> LENGTH: 36
<212> TYPE: PRT
<213> ORGANISM: Homo sapiens

<400> SEQUENCE: 8

Gly Cys Gly Phe Leu Gly Phe Tyr His Val Gly Ala Thr Arg Cys Leu
  1               5                  10                  15

Ser Glu His Ala Pro His Leu Leu Arg Asp Ala Arg Met Leu Phe Gly
            20                  25                  30

Ala Ser Ala Gly
        35


<210> SEQ ID NO 9
<211> LENGTH: 17
<212> TYPE: PRT
<213> ORGANISM: Homo sapiens

<400> SEQUENCE: 9

Cys Arg Leu Glu Gly Asp Glu Leu Leu Asp His Leu Arg Leu Ser Ile
  1               5                  10                  15

Leu


<210> SEQ ID NO 10
<211> LENGTH: 6
<212> TYPE: PRT
<213> ORGANISM: Artificial Sequence
<220> FEATURE:
<223> OTHER INFORMATION: Description of Artificial Sequence: synthetic
      six His tag

<400> SEQUENCE: 10

His His His His His His
  1               5


<210> SEQ ID NO 11
<211> LENGTH: 6
<212> TYPE: PRT
<213> ORGANISM: Homo sapiens

<400> SEQUENCE: 11

Gly Cys Gly Phe Leu Gly
  1               5
```

<210> SEQ ID NO 12
<211> LENGTH: 5
<212> TYPE: PRT
<213> ORGANISM: Homo sapiens

<400> SEQUENCE: 12

Gly Ala Ser Ala Gly
1 5

<210> SEQ ID NO 13
<211> LENGTH: 42
<212> TYPE: DNA
<213> ORGANISM: Artificial Sequence
<220> FEATURE:
<223> OTHER INFORMATION: Description of Artificial Sequence: synthetic primer

<400> SEQUENCE: 13
aaagaattcc accatgtacg acgcagagcg cggctggagc tt 42

<210> SEQ ID NO 14
<211> LENGTH: 50
<212> TYPE: DNA
<213> ORGANISM: Artificial Sequence
<220> FEATURE:
<223> OTHER INFORMATION: Description of Artificial Sequence: synthetic primer

<400> SEQUENCE: 14
aaaagtcgac tcagtgatgg tgatggtgat gcagactctt ctctagtgaa 50

<210> SEQ ID NO 15
<211> LENGTH: 24
<212> TYPE: DNA
<213> ORGANISM: Artificial Sequence
<220> FEATURE:
<223> OTHER INFORMATION: Description of Artificial Sequence: synthetic primer

<400> SEQUENCE: 15
ggcaaaatag gcatctctct tacc 24

<210> SEQ ID NO 16
<211> LENGTH: 22
<212> TYPE: DNA
<213> ORGANISM: Artificial Sequence
<220> FEATURE:
<223> OTHER INFORMATION: Description of Artificial Sequence: synthetic primer

<400> SEQUENCE: 16
ggagggataa ggccactgta ga 22

<210> SEQ ID NO 17
<211> LENGTH: 28
<212> TYPE: DNA
<213> ORGANISM: Artificial Sequence
<220> FEATURE:
<223> OTHER INFORMATION: Description of Artificial Sequence: synthetic primer

<400> SEQUENCE: 17
aacataccaa ggcatccacg acttcgtc 28

-continued

```
<210> SEQ ID NO 18
<211> LENGTH: 18
<212> TYPE: DNA
<213> ORGANISM: Artificial Sequence
<220> FEATURE:
<223> OTHER INFORMATION: Description of Artificial Sequence: synthetic
      primer

<400> SEQUENCE: 18

actgcacgcg gtcacctt                                               18


<210> SEQ ID NO 19
<211> LENGTH: 21
<212> TYPE: DNA
<213> ORGANISM: Artificial Sequence
<220> FEATURE:
<223> OTHER INFORMATION: Description of Artificial Sequence: synthetic
      primer

<400> SEQUENCE: 19

cacgaggtcc atgaggatct c                                           21


<210> SEQ ID NO 20
<211> LENGTH: 28
<212> TYPE: DNA
<213> ORGANISM: Artificial Sequence
<220> FEATURE:
<223> OTHER INFORMATION: Description of Artificial Sequence: synthetic
      primer

<400> SEQUENCE: 20

tgtgcagtct ccctctcggc cgtataat                                    28
```